(12) United States Patent
Afonina et al.

(10) Patent No.: US 9,677,142 B2
(45) Date of Patent: Jun. 13, 2017

(54) DETECTION OF METHICILLIN-RESISTANT STAPHYLOCOCCUS AUREUS

(75) Inventors: Irina A. Afonina, Mill Creek, WA (US); Yevgeniy S. Belousov, Mill Creek, WA (US); Walt Mahoney, Woodinville, WA (US)

(73) Assignee: ELITECHGROUP B.V., Spankeren (NL)

( * ) Notice: Subject to any disclaimer, the term of this patent is extended or adjusted under 35 U.S.C. 154(b) by 1169 days.

(21) Appl. No.: 13/479,557

(22) Filed: May 24, 2012

(65) Prior Publication Data

US 2015/0275274 A1    Oct. 1, 2015

Related U.S. Application Data

(60) Provisional application No. 61/489,614, filed on May 24, 2011, provisional application No. 61/532,454, filed on Sep. 8, 2011, provisional application No. 61/614,381, filed on Mar. 22, 2012.

(51) Int. Cl.
*C12Q 1/68* (2006.01)
*C07H 21/04* (2006.01)

(52) U.S. Cl.
CPC ............. *C12Q 1/689* (2013.01); *C12Q 1/686* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,128,179 A | 4/1964 | Kendall et al. |
| 3,194,805 A | 7/1965 | Brooker et al. |
| 3,996,345 A | 12/1976 | Ullman et al. |
| 4,351,760 A | 9/1982 | Khanna et al. |
| 4,683,195 A | 7/1987 | Mullis et al. |
| 4,683,202 A | 7/1987 | Mullis |
| 4,965,188 A | 10/1990 | Mullis et al. |
| 5,187,288 A | 2/1993 | Kang et al. |
| 5,188,934 A | 2/1993 | Menchen et al. |
| 5,227,487 A | 7/1993 | Haugland et al. |
| 5,248,782 A | 9/1993 | Haugland et al. |
| 5,304,645 A | 4/1994 | Klein et al. |
| 5,433,896 A | 7/1995 | Kang et al. |
| 5,442,045 A | 8/1995 | Haugland et al. |
| 5,492,806 A | 2/1996 | Drmanac et al. |
| 5,525,464 A | 6/1996 | Drmanac et al. |
| 5,556,752 A | 9/1996 | Lockhart et al. |
| 5,556,959 A | 9/1996 | Brush et al. |
| 5,583,236 A | 12/1996 | Brush |
| 5,808,044 A | 9/1998 | Brush et al. |
| 5,852,191 A | 12/1998 | Karandikar et al. |
| 5,986,086 A | 11/1999 | Brush et al. |
| 5,994,056 A | 11/1999 | Higuchi |
| 6,020,481 A | 2/2000 | Benson et al. |
| 6,127,121 A | 10/2000 | Meyer, Jr. et al. |
| 6,156,507 A | 12/2000 | Hiramatsu et al. |
| 6,162,931 A | 12/2000 | Gee et al. |
| 6,171,785 B1 | 1/2001 | Higuchi |
| 6,180,295 B1 | 1/2001 | Helber et al. |
| 6,221,604 B1 | 4/2001 | Upadhya et al. |
| 6,569,627 B2 | 5/2003 | Wittwer et al. |
| RE38,416 E | 2/2004 | Petrie et al. |
| 6,727,356 B1 | 4/2004 | Reed et al. |
| 6,790,945 B2 | 9/2004 | Lukhtanov et al. |
| 6,946,267 B2 | 9/2005 | Liu et al. |
| 6,949,367 B1 | 9/2005 | Dempcy et al. |
| 7,348,146 B2 | 3/2008 | Belousov et al. |
| 7,671,218 B2 | 3/2010 | Lukhtanov et al. |
| 7,767,834 B2 | 8/2010 | Lukhtanov et al. |
| 7,838,221 B2 | 11/2010 | Huletsky et al. |
| 2005/0118623 A1 | 6/2005 | Belousov et al. |
| 2007/0048758 A1* | 3/2007 | Lokhov ................. C12P 19/34 435/6.12 |
| 2010/0047267 A1* | 2/2010 | Masignani ........... A61K 39/085 424/190.1 |

FOREIGN PATENT DOCUMENTS

| | | |
|---|---|---|
| EP | 1314734 | 5/2003 |
| EP | 1408366 | 4/2004 |
| JP | 2010-512799 A | 4/2010 |

(Continued)

OTHER PUBLICATIONS

Francois (Journal of Clinical Microbiology Jan. 2003 pp. 254-260).*
Richardson (Science Mar. 31, 2008 vol. 319 pp. 1672-1676).*
GenBank (Accession X52593.1 GI 46610 Apr. 18, 2005).*
Huletsky (Journal of Clinical Microbiology May 2004 col. 42 No. 5 pp. 1875-1884).*
Paule (American Journal of Clinical Pathology 2005 vol. 124 pp. 404-407).*
Jukes (Journal of Medical Microbiology 2010 vol. 59 pp. 1456-1461).*
Bengtsson, Martin, et al; A New Minor Groove Binding Asymmetric Cyanine Reporter Dye for Real-Time PCR; Nucleic Acids Research, vol. 31, No. 8, 2003.
Blanc, D.S., et al; High Proportion of Wrongly Identified Methicillin-Resistant *Staphyloccus aureus* Carriers by Use of a Rapid Commercial PCR Assay Due to Presence of Staphylococcal Cassette Chromosome Element Lacking the mecA Gene; J. Clin. Microbiol., 49, 2, 722-724, Feb. 2011.

(Continued)

*Primary Examiner* — Amanda Haney
(74) *Attorney, Agent, or Firm* — Jackson Walker LLP

(57) ABSTRACT

The present methods pertain to amplifying and/or detecting *Staphylococcus aureus* ("SA") and methicillin-resistant *Staphylococcus aureus* ("MRSA") nucleic acids based on a combined detection of ldh1 as a SA marker and mecA as a MRSA marker. In certain embodiments the methods also pertain to amplifying and/or detecting one or more SCCmec integration sites or bridge regions. Primers and probes are suitable to be used in the present methods to detect SA and MRSA simultaneously in a single reaction or in separate reactions. The amplified nucleic acid can be detected by a variety of state of the art methods, including fluorescence resonance energy transfer ("FRET"), radiolabels, enzyme labels, and the like.

17 Claims, 4 Drawing Sheets

(56) References Cited

FOREIGN PATENT DOCUMENTS

| WO | 92/10588 | 6/1992 |
| WO | 96/17957 | 6/1996 |
| WO | 02/062816 | 8/2002 |
| WO | 03/023357 | 3/2003 |
| WO | 2008/140612 | 11/2008 |
| WO | 2008/140612 A2 | 11/2008 |
| WO | 2009/086218 | 7/2009 |
| WO | 2009/086218 A2 | 7/2009 |
| WO | 2010/146349 | 12/2010 |

OTHER PUBLICATIONS

Bolli, M., et al; Watson-Crick Base-Pairing Properties of Bicyclo-DNA, Nucleic Acids Research, vol. 24, No. 23, 4660-4667, 1996.
Boucher, H., et al; Serious Infections Caused by Methicillin-Resistant *Staphylococcus aureus*; CID, 51 (Supplement 2), S183-S-197, 2010.
Brown, J., et al; Impact of Rapid Methicillin-Resistant *Staphylococcus aureus* Polymerase Chain Reaction Testing on Mortality and Cost Effectiveness in Hospitalized Patients With Bacteraemia: A Decision Model, vol. 28, Issue 7, 567-575, Jul. 1, 2010 (abstract).
Chen, Jer-Kang, et al; Synthesis of Oligodeoxyribonucleotide N3'-P5' Phosphoramidates; Nucleic Acids Research, vol. 23, No. 14, 2661-2668, 1995.
Hartman, B.J., et al; Low-Affinity Penicillin-Binding Protein Associated With Beta-Lactam Resistance in *Staphylococcus aureus*; Journal of Bacteriology; vol. 158, No. 2, 513-516, 1984.
Haugland, R.P., Handbook of Fluorescent Probes and Research Chemicals, Sixth Edition, Molecular Probes, 3 pages,1996.
Hiramatsu, K., et al; Molecular Genetics of Methicillin-Resistant *Staphylococcus aureus*; Int. J. Med. Microbiol., 292, 2, 67-74, Jul. 2002 (abstract).
Huletsky, A., et al; Identification of Methicillin-Resistant *Staphylococcus aureus* Carriage in Less Than 1 Hour During a Hospital Surveillance Program; CID, 40, 976-981, Apr. 1, 2005.
Innis, M.A., et al; PCR Protocols a Guide to Methods and Applications, 1990.
Kolman, S., et al; Evaluation of Single and Double-Locus Real-Time PCR Assays for Methicillin-Resistant *Staphylococcus aureus* (MRSA) Surveillance; BMC Research Notes; 3, 110, 2010.
Palissa, M., et al; Reduction of Protected 2'-Chloro-2'-Deoxy-Dinucleotides With Tri-N-butyltinhydride; Z. Chem., 27, 216, 1987.
Richardson, A.R., et al; A Nitric Oxide-Inducible Lactate Dehydrogenase Enables *Staphylococcus aureus* to Resist Innate Immunity; Science, vol. 319, 1672, Mar. 21, 2008.
Rossney, A.S., et al; Evaluation of the Xpert Methicillin-Resistant *Staphylococcus aureus* (MRSA) Assay Using the Genexpert Real-Time PCR Platform for Rapid Detection of MRSA From Screening Specimens, J. Clin. Microbio., 46, 10, 3285-3290, Aug. 6, 2008.
Sambrook, J., et al; Molecular Cloning: A Laboratory Manual, Second Edition, Cold Spring Harbor Laboratory Press, 1989.
Sherlock, O., et al; MRSA Screening: Can One Swab Be Used for Both Culture and Rapid Testing? An Evaluation of Chromogenic Culture and Subsequent Hain Genoquick PCR Amplification/Detection; European Society of Clinical Microbiology and Infectious Diseases; 16, 955-959, 2010.
Singh, Sanjay K., et al; LNA (Locked Nucleic Acids): Synthesis and High-Affinity Nucleic Acid Recognition; Chem. Comm., 455-456, 1998.
Stevenson, J., et al; Effect of Sequence Polymorphisms on Performance of Two Real-Time PCR Assays for Detection of Herpes Simplex Virus; J. Clin. Microbiol., 43, 5, 2391-2398, 2005.
Warren, D.K., et al; Detection of Methicillin-Resistant *Staphylococcus aureus* Directly From Nasal Swab Specimens by a Real-Time PCR Assay; Journal of Clinical Microbiology, vol. 42, No. 12, 5578-5581, 2004.
Wengel, J.; Synthesis of 3'-C- and 4'-C-Branched Oligonucleotides and the Development of Locked Nucleic Acid (LNA); Acc. Chem. Res., 32, 301-310, 1999.
Whitaker, J.E., et al; Fluorescent Rhodol Derivatives: Versatile, Photostable Labels and Tracers; Anal Biochem., 207(2), 267-279, Dec. 1992 (abstract).
Wong, H., et al; Characterization of *Staphylococcus aureus* Isolates With a Partial or Complete Absence of Staphylococcal Cassette Chromosome Elements; J. Clin. Microbiol., 48 (10), 3525-3531, Jul. 28, 2010.
Garcia-Alvarez, L. et al; Meticillin-Resistant *Staphylococcus aureus* With a Novel mecA in Human and Bovine Populations in the UK and Denmark: A Descriptive Study; Lancet Infection Dis., vol. 11, Jun. 3, 2011, pp. 595-603.
Sabet, Negar Shafiei, et al; Simultaneous Species Identification and Detection of Methicillin Resistance in Staphylococci Using Triplex Real-Time PCR Assay; Diagnostic Microbiology and Infectious Diseases, vol. 56, No. 1, Sep. 1, 2006, pp. 13-18.
Stegger, M, et al; Rapid Detection, Differentiation and Typing of Methicillin-Resistant *Staphylococcus aureus* Harbouring Either mecA or the New Meca Homologue mecALGA251; Clinical Microbiology and Infection; vol. 18, No. 4, Nov. 7, 2011, pp. 395-400.
European Patent Office; International Search Report and Written Opinion; PCT Application No. PCT/US2012/039275; Jun. 27, 2013.
European Patent Office; Response to Rule 161 Communication; European Application No. 12815869.8, Jul. 17, 2014.
Canadian Patent Office; Response to Office Action; Canadian Patent Application No. 2,835,283, Aug. 11, 2015.
European Patent Office; Extended European Search Report; European Application No. 14179255.6; Oct. 15, 2014.
Canadian Patent Office; Office Action; Canadian Patent Application No. 2,835,283, Feb. 16, 2015.
The Examiner's Report issued by Canadian Intellectual Property Office on May 4, 2016 for the copending Canadian patent application No. 2,835,283.
The Office action issued by the Japanese Patent Office on Jun. 7, 2016 for the corresponding Japanese patent application No. 2014-512092, and its English translation.
Francois et al., "Rapid Detection of Methicillin-Resistant *Staphylococcus aureus* Directly from Sterile or Nonsterile clinical Samples by a New Molecular Assay", J. Clin. Mocrobiol., 2003, vol. 41, No. 1, pp. 254-260.
Sabet et al., "Simultaneous Species Identification and Detection of Methicillin Resistance in Staphylococci using Triplex Real-Time PCR Assay.", Diagnostic Microbiology and Infectious Disease, 2006, vol. 56, pp. 13-18.
Richardson et al., "A Nitric Oxide-Inducible Lactate Dehydrogenase Enables *Staphylococcus aureus* to Resist Innate Immunity", Science, 2008, vol. 319, No. 5870, pp. 1672-1676.
Stegger et al., "Rapid Detection, Differentiation and Typing of Methicillin-resistant *Staphylococcus aureus* Harbouring either mecA of the new mecA homologue mecALGA251", Clinical Microbiology and Infection, 2011, vol. 18, No. 4, pp. 395-400.
Garcia-Alvarez et al., "Meticillin-Resistant *Staphylococcus aureus* with a Novel mecA homologue in Human and Bovine Populations in the UK and Denmark; a Descriptive Study", Lancet Infect Dis., 2011, vol. 11, No. 8, pp. 595-603.
The Amendment and argument filed with the Japanese Patent Office on Aug. 23, 2016 for the corresponding Japanese patent application No. 2014-512092, and the English translation of Amendment.
The English translation of the Decision of Refusal issued by the Japanese Patent Office on Jan. 10, 2017 for the corresponding Japanese patent application No. 2014-512092.
The Decision of Refusal issued by the Japanese Patent Office on Jan. 10, 2017 for the corresponding Japanese patent application No. 2014-512092, and its Summary in English.
Hafez et al., "The effect of the mecA gene and its mutant form on the response of *S. aureus* to the most common antibiotics", Int. J. Immunological studies, 2009, vol. 1, No. 1, pp. 106-122.
Afonina et al., "Primers with 5' flaps improve real-time PCR", BioTechniques, 2007, vol. 43, No. 6, p. 770-774.

\* cited by examiner

DETECTION OF METHICILLIN-RESISTANT *STAPHYLOCOCCUS AUREUS*

This application claims priority to U.S. Provisional Patent Application Ser. Nos. 61/489,614, filed May 24, 2011, 61/532,454, filed Sep. 8, 2011, and 61/614,381, filed Mar. 22, 2012, all entitled "Detection of Methicillin-Resistant *Staphylococcus Aureus*," the entire contents of which are hereby incorporated by reference.

BACKGROUND

This disclosure relates to bacterial diagnostics, and more particularly to the detection of methicillin-resistant *Staphylococcus aureus*.

The widespread emergence of methicillin-resistant *Staphylococcus aureus* ("MRSA") is a serious clinical problem world wide. *S. aureus* and especially MRSA today is viewed as one of the major causes of both health care-associated and community associated infections. *S. aureus* is a commensal bacterium that colonizes the nasal passages, vagina, pharynx, axcillae and/or damaged skin surfaces. Infections can occur with a skin or mucosal breach allowing the access to adjoining tissues and blood stream. Risk is increased by the presence of catheters. *S. aureus* is unique in its ability to invade normal tissue and cause disease in previously normal tissues at virtually all sites (Boucher et al., CID, 51 (Supplement2): S183-S197, 2010). MRSA causes various infections, for example skin and soft tissues infections, blood-borne infections and pneumonia (Gemmel et al., J. Antimicrob. Chemother., 57: 589-608, 2006). The emergence of *S. aureus* strains which are resistant to antibiotics poses a challenge to successful treatment. It is viewed that patients hospitalized with *S. aureus* bacteremia have an unacceptably high mortality rate. Literature available today has indicated that timely selection of the most appropriate antibacterial treatment may reduce mortality. One tool that may help with the selection is rapid distinction of MRSA from methicillin-susceptible *aureus* ("MSSA") (Brown et al., Pharmacoeconomics, 28: 567-575, 2010).

Although some tools and assays exist for the identification of MRSA, they are less than ideal. As high as 12.9% false positives have been reported for a single-locus commercially available assay (Blanc et al., J. Clin. Microbiol., 49: 722-724, 2011). An evaluation of two single and one double-locus real-time PCR assays for MRSA warns about the high prevalence of "false negatives" and "false positives" (Kolman et al., BMC Res. Notes, 3; 110, 2010). There clearly exits a need for improved MRSA assays.

SUMMARY

The present disclosure provides methods, probes, and primers for the detection of *Staphylococcus aureus* ("SA") and methicillin-resistant *Staphylococcus aureus* ("MRSA") in samples including biological samples (e.g., blood, nasopharyngeal or throat swab, stool, wound swab, or other tissue).

L-Lactate production allows *S. aureus* to maintain redox homeostasis during nitrosative stress and is essential for virulence. Nitric oxide (NO*)-inducible lactate dehydrogenase activity and NO* resistance distinguish *S. aureus* from the closely related commensal species *S. epidermidis* and *S. saprophyticus* (Richardson et al., Science, 319: 1672, 2008).

The resistance to β-lactam antibiotics is caused by an altered penicillin-binding protein (PBP2a) encoded by the mecA gene (Hartman & Tomasz, J. Bacteriol., 158: 513-516, 1984). This resistance determinant resides on a mobile genetic element called the staphylococcal cassette chromosome mec (SCCmec) that integrates downstream of a *S. aureus*-specific open reading frame (orfX) (Hiramatsu et al., Int. J. Me. Microbiol., 292:67-74, 2002). The detection of MRSA by PCR targeting the SCCtneclorfX junction was proposed by Huletsky et al (J. Clin. Microbiol., 42: 1875-1884, 2004). Since mecA resides on SCCmec, detection of the SCCmeclorfX junction is viewed as a surrogate for the detection of MRSA. A number of commercial MRSA assay are in the market based on the site specific integration of SCCmec at orfX, namely the GENEXPERT. Cepheid, Sunnyvale, Calif. (Rossney et al., J. Clin. Microbiol., 46:3285-3290, 2008), the IDI-MRSA assay (Warren et al., J. Clin Microbiol., 42: 5578-5581, 2004) and Hain GENO-QUICK MRSA assay, Hain Lifescience GmbH, Nehren, Denmark (Sherlock et al., Clin. Microbiol. Infect. 16:955-959, 2010). Shortly after the introduction of these assays reports of "false positives" were reported. These occur when assays identify as MRSA-positive specimens that contain only methicillin susceptible strains of *S. aureus* (Wong et al. J. Clin. Microbiol., 48: 3525-3531, 2010). It is now known that "false positive" results in single-locus PCR assays are due to partial SCCmec deletions.

In the present disclosure, the nucleic acids present in a clinical or test sample obtained from a biological sample or tissue suspected of containing the SA and MRSA are extracted from the samples with methods known in the art. The nucleic acids are amplified and SA and MRSA nucleic acid detected. More specifically in the case of SA that is not MRSA the lactate dehydrogenase 1 gene (ldh1), but not mecA, is detected, or detected in different quantities; and in the case of MRSA the ldh1 and mecA genes are detected in equal amount. The amplified nucleic acid can be detected by a variety of state of the art methods, including fluorescence resonance energy transfer ("FRET"), radiolabels, enzyme labels, and the like. The amplified nucleic acids can also be detected by any combination of detection techniques that may include hybridization detection probes and/or primers.

In one aspect, this disclosure provides a method for detecting SA and MRSA in a biological sample from an individual. The disclosure also provides oligonucleotide primers and probes comprising nucleotide sequences characteristic of *Staphylococcus aureus* ("SA") and methicillin-resistant *Staphylococcus aureus* ("MRSA") genomic nucleic acid sequences. The method includes performing at least one cycling step of amplification and hybridization. The amplification step includes contacting the sample nucleic acid with pairs of primers to produce amplification product(s) if the SA and/or mecA nucleic acid is present. The preferred primers target a specific region of the lactate dehydrogenase 1 gene (ldh1; SA) and the mecA gene (methicillin resistance). The oligonucleotide probes detect the amplified target directly or indirectly. The preferred oligonucleotide probe is a 5'-minor groove binder-fluorophore-oligonucleotide-quencher-3' conjugate that fluoresces upon hybridization to its complementary amplified target. In some embodiments one or more primer(s) are labeled. En some embodiments the probe(s) is omitted. In some embodiments an internal control is provided.

In one embodiment the method comprises the detection of ldh1 and mecA genes.

Kits are further provided for the detection of *Staphylococcus aureus* (SA) and methicillin-resistant *Staphylococcus aureus* (MRSA) in biological samples comprising at least one annealing oligonucleotide specific for the amplification of SA sequences and comprising at least one oligonucleotide specific for the detection of mecA sequences.

The method further includes detecting of the presence or absence of a fluorescent signal (e.g., a signal resulting from FRET) of the hybridization probes or primers. The presence of the fluorescent signal due to a first label usually indicates the presence of SA and the detection of the fluorescent signal due to a second label indicates the presence of a mecA gene in the biological sample, while the absence of the signal usually due to the first label indicates the absence of SA and the absence of signal due to the second label indicates the absence of mecA in the biological sample.

The method can additionally include determining the melting temperature profile between the probes and the amplification products or amplicons in the case of labeled primers(s). The melting curves further confirm the presence or absence of SA and mecA as well as the potential presence of SA and mecA mutants, with mismatch(es) in the probe sequence area or in the amplicon in the case of labeled primer(s).

The method can additionally include determining the mixed infection where ldh1 and mecA signals come from different organisms by comparing relative quantities of ldh1 and mecA markers. Equal quantities suggest MRSA infection while different quantities suggest a mixed infection of MRSA-negative S. aureus and other than S. aureus mecA-carrier.

The present method allows the specific, sensitive, and rapid detection of SA and MRSA. MRSA infection is often not clinically distinguishable from other mecA carrying bacteria and other viral pathogens for which specific therapies are available. The present methods overcome this problem in diagnosis, by providing rapid specific detection of SA and MRSA, thereby eliminating false positive results observed in some of the assays in the art. In addition, the hybridization-based probes or labeled primer(s) allow melting curve analysis, which can identify potential new mutants of ldh1 and mecA.

In another embodiment the method comprises the detection of $mecA_{LGA251}$, mecA and ldh1 genes.

In one method, $mecA_{LGA251}$ and mecA are labeled with the same fluorescent dye, and in another method they are labeled with different dyes.

In another embodiment the method comprises the detection of the dl gene, SCCmec, and SCCmec integration site(s) or bridge region.

In another embodiment the method comprises the detection of the ldh1 gene, SCCmec integration site(s) or bridge region and mecA.

In one embodiment the method comprises the detection of the ldh1 gene and at least one SCCmec integration site(s) or bridge region.

Other objects, features, and advantages will be apparent to one of skill in the art from the following detailed description and figures.

DETAILED DESCRIPTION

I. General

Figure 1:
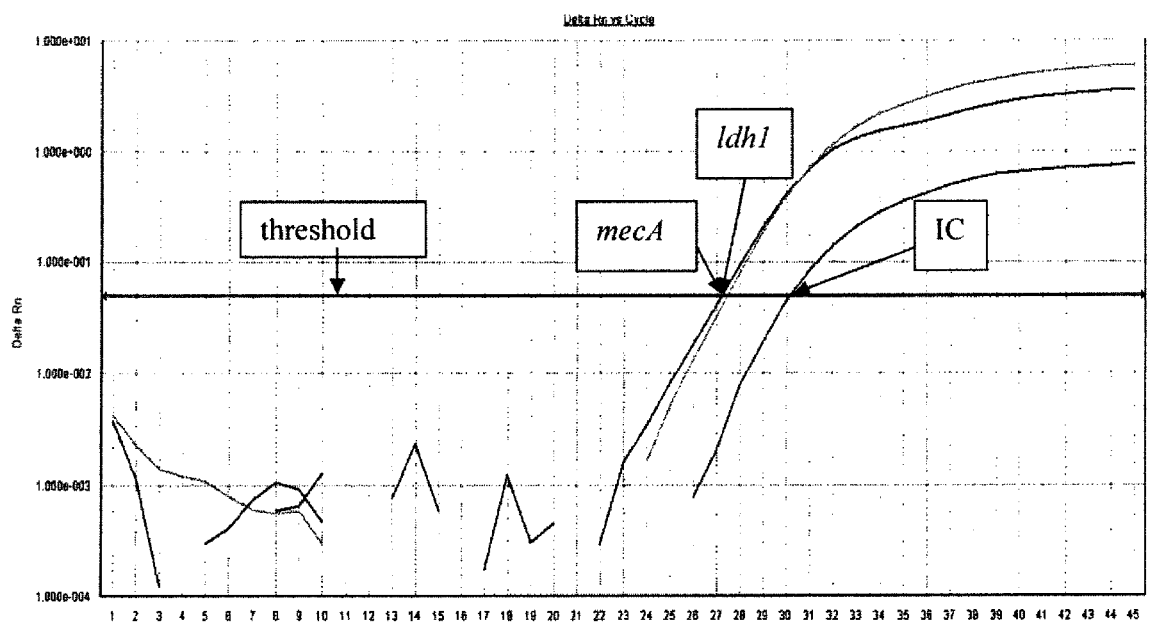
FIG. 1 illustrates the real-time detection of ldh1, mecA, and internal control (IC) in a MRSA-positive sample.

The present disclosure provides methods, probes, and primers for the detection of Staphylococcus aureus (SA) and methicillin-resistant Staphylococcus aureus (MRSA). The methods and compositions disclosed are highly specific for SA and MRSA with high sensitivity, specificity, and speed that allow the detection of clinical relevant levels. The methods and compositions can conveniently be used to amplify and/or detect SA and mecA in samples. In some embodiments mecA is detected in bacteria other than S. aureus.

II. Definitions

A "sample" as used herein refers to a sample of any source which is suspected of containing S. aureus. These samples can be tested by the methods described herein. A sample can be from a laboratory source or from a non-laboratory source. A sample may be suspended or dissolved in liquid materials such as buffers, extractants, solvents, and the like. Samples also include biological samples such as animal and human tissue or fluids such as whole blood, blood fractions, serum, plasma, cerebrospinal fluid, lymph fluids, milk, urine, various external secretions of the respiratory, intestinal, and genitourinary tracts, tears, and saliva; and biological fluids such as cell extracts, cell culture supernatants, fixed tissue specimens, and fixed cell specimens. Samples include nasopharyngeal or throat swabs, stools, wound or rectal swabs. Biological samples may also include sections of tissues such as biopsy and autopsy samples or frozen sections taken for histological purposes. A biological sample is obtained from any animal including, e.g., a human.

Quantities are define different as described in Quality Control for Molecular Diagnostics Organization (www.qc-md.org) where the organization considers reported quantities different if they are not within 0.5 log 10 copies which in the case of $C_q$s (or $C_t$s) corresponds to $\Delta C_q \geq 2$.

The terms "flap primer" or "overhang primer" refer to a primer comprising a 5' sequence segment non-complementary to a target nucleic acid sequence (e.g., ldh1 or mecA nucleic acid sequence) and a 3' sequence segment complementary to the target nucleic acid sequence (e.g., a mecA or ldh1 nucleic acid sequence). The flap primers are suitable for primer extension or amplification of the target nucleic acid sequence (e.g., mecA or ldh1 nucleic acid sequence). The primers may comprise one or more non-complementary or modified nucleotides (e.g., pyrazolopyrimidines as described herein below) at any position including, e.g., the 5' end.

The term "fluorescent generation probe" refers either to a) an oligonucleotide having an attached minor groove binder, fluorophore, and quencher, b) an oligonucleotide having an attached fluorophore, and quencher, c) an oligonucleotide having an attached minor groove binder, and fluorophore, d) an oligonucleotide having an attached fluorophore and quencher or e) a DNA binding reagent. The probes may comprise one or more non-complementary or modified nucleotides (e.g., pyrazolopyrimidines as described herein below) at any position including, e.g., the 5' end. In some embodiments, the fluorophore is attached to the modified nucleotide. In some embodiments the probe is cleaved to yield a fluorescent signal.

The terms "fluorescent label" or "fluorophore" refer to compounds with a fluorescent emission maximum between about 400 and about 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO®-1 (533), JOE (548), BODIPY® 530/550 (550), DiI (565), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642), C-Phycocyanin (648), TO-PRO™-3 (660), TOTO®-3 (660), DiD DilC(5) (665), Cy5™ (670), Thiadicarbocyanine (671), and Cy5.5 (694). Additional fluorophores are disclosed in PCT Patent Publication No. WO 03/023357 and U.S. Pat. No. 7,671,218. Examples of these and other suitable dye classes can be found in Haugland et al., HANDBOOK OF FLUORESCENT PROBES AND RESEARCH CHEMICALS, SIXTH ED., Molecular Probes, Eugene, Ore. (1996); U.S. Pat. Nos. 3,194,805; 3,128,179; 5,187,288; 5,188,934; 5,227,487; 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Smith et al., *J. Chem. Soc. Perkin Trans.* 2:1195-1204 (1993); Whitaker, et al., *Anal. Biochem.* 207:267-279 (1992); Krasoviskii and Bolotin, ORGANIC LUMINESCENT MATERIALS, VCH Publishers, N.Y. (1988); Zolliger, COLOR CHEMISTRY, 2$^{nd}$ Edition, VCH Publishers, N.Y. (1991); Hirschberg et al., *Biochemistry* 37:10381-10385 (1998); Fieser and Fieser, REAGENTS FOR ORGANIC SYNTHESIS, Volumes 1 to 17, Wiley, US (1995); and Geiger et al., *Nature* 359:859-861 (1992). Still other dyes are provided via online sites such as zeiss.com. Phosphonate dyes are disclosed in co-owned U.S. Pat. No. 7,671,218 and U.S. Pat. No. 7,767,834.

There is extensive guidance in the art for selecting quencher and fluorophore pairs and their attachment to oligonucleotides (Haugland, 1996; U.S. Pat. Nos. 3,996,345 and 4,351,760 and the like). Preferred quenchers are described in U.S. Pat. No. 6,727,356, incorporated herein by reference. Other quenchers include bis azo quenchers (U.S. Pat. No. 6,790,945) and dyes from Biosearch Technologies, Inc. (provided as Black Hole™ Quenchers: BH-1, BH-2 and BH-3), Dabcyl, TAMRA and carboxytetramethyl rhodamine.

The term "linker" refers to a moiety that is used to assemble various portions of the molecule or to covalently attach the molecule (or portions thereof) to a solid support. Typically, a linker or linking group has functional groups that are used to interact with and form covalent bonds with functional groups in the ligands or components (e.g., fluorophores, oligonucleotides, minor groove binders, or quenchers) of the conjugates described and used herein. Examples of functional groups on the linking groups (prior to interaction with other components) include —NH$_2$, —NHNH$_2$, —ONH$_2$, —NHC=(O)NHNH$_2$, —OH, and —SH. The linking groups are also those portions of the molecule that connect other groups (e.g., phosphoramidite moieties and the like) to the conjugate. Additionally, a linker can include linear or acyclic portions, cyclic portions, aromatic rings, and combinations thereof.

The term "solid support" refers to any support that is compatible with oligonucleotide synthesis, including, for example, glass, controlled pore glass, polymeric materials, polystyrene, beads, coated glass, and the like.

In the description herein, the abbreviations M, FL, Q, CPG, and ODN refer to "minor groove binder," "fluorescent label" or "fluorophore," "quencher," "controlled pore glass" (as an example of a solid support), and "oligonucleotide" moieties or molecules, respectively, and in a manner which is apparent from context. The terms "probe" and "conjugate" are used interchangeably and refer to an oligonucleotide having an attached minor groove binder, fluorophore, and quencher.

The terms "oligonucleotide," "nucleic acid," and "polynucleotide" are used interchangeably herein. These terms refer to a compound comprising nucleic acid, nucleotide, or its polymer in either single- or double-stranded form, e.g., DNA, RNA, analogs of natural nucleotides, and hybrids thereof. The terms encompass polymers containing modified or non-naturally-occurring nucleotides, or to any other type of polymer capable of stable base-pairing to DNA or RNA including, but not limited to, peptide nucleic acids as described in Nielsen et al., *Science*, 254:1497-1500 (1991), bicyclo DNA oligomers as described in Bolli et al., *Nucleic Acids Res.*, 24:4660-4667 (1996), and related structures. Unless otherwise limited, the terms encompass known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). A "subsequence" or "segment" refers to a sequence of nucleotides that comprise a part of a longer sequence of nucleotides.

The practice of the methods described herein will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

III. Description

The present methods pertain to amplifying and/or detecting SA and MRSA nucleic acids based on a combined detection of ldh1 as a SA marker and mecA as a methicillin resistance marker. Primers and probes are suitable to be used in the present methods to detect SA and MRSA simultaneously in a single reaction or in separate reactions. Typically, the methods are performed on genomic DNA, which is in turn amplified with any DNA-based amplification method.

One such amplification method is the polymerase chain reaction (see, e.g., U.S. Pat. Nos. 4,683,195 and 4,965,188 Mullis e al, *Cold Spring Harb. Symp. Quant. Biol.,* 51 Pt 1:263-273 (1986)). The amplifications are performed using reagents which are currently commercially available from several vendors (e.g., Life Technologies; Carlsbad, Calif.; and Qiagen; Valencia, Calif.).

Amplification of DNA templates using reactions is well known (see, e.g., U.S. Pat. Nos. 4,683,195 and 4,683,202; PCR PROTOCOLS: A GUIDE TO METHODS AND APPLICATIONS (Innis et al., eds, 1990)). Methods such as polymerase chain reaction ("PCR") and ligase chain reaction ("LCR") can be used to amplify nucleic acid sequences of ldh1/mecA target sequences directly from a sample suspected of containing the target sequences. The reaction is preferably carried out in a thermal cycler to facilitate incubation times at desired temperatures. Degenerate oligonucleotides can be designed to amplify target DNA sequence homologs using the known sequences that encode the target DNA sequence.

Exemplary PCR reaction conditions typically comprise either two or three step cycles. Two-step cycles have a denaturation step followed by a hybridization/elongation step. Three step cycles comprise a denaturation step followed by a hybridization step followed by a separate elongation step. For PCR, a temperature of about 36° C. is typical for low stringency amplification, although annealing temperatures may vary between about 32° C. and 48° C., depending on primer length. For high stringency PCR amplification, a temperature of about 62° C. is typical, although high stringency annealing temperatures can range from about 50° C. to about 65° C., depending on primer length and specificity. Typical cycle conditions for both high and low stringency amplifications include a denaturation phase of about 90° C.-95° C. for 0 seconds–15 minutes, an annealing phase of about 56-60° C. for 0 seconds-2 minutes, and an extension phase of about 72-76° C. for 0 seconds-2 minutes. A preferred cycle protocol has a denaturation phase of 93° C. for 10 seconds, an annealing phase of 56° C. for 30 seconds, and an extension phase of 72° C. for 15 seconds.

Generally, the present method is for detecting methicillin-resistant *Staphylococcus aureus* in a sample containing nucleic acids by amplifying the nucleic acids in the sample and then detecting nucleic acids in the sample comprising amplified mecA and ldh1 genes. The presence of amplified mecA and ldh1 genes in equal quantity indicates the presence of methicillin-resistant *Staphylococcus aureus.*

Accordingly, in one aspect, an example of the present method for detecting a ldh1 and mecA nucleic acid in a sample comprises:

(a) contacting a sample suspected of containing the ldh1 nucleic acid with a first flap primer and a second flap primer having the formula:

5'-(X)$_n$Y-3'  (I), wherein X represents the 5' portion of the flap primer that is non-complementary to the SA nucleic acid and n=0 or 1, Y represents the 3' portion of the flap primer that is complementary to the ldh1 nucleic acid, wherein X is about 3-30 nucleotides in length, (b) contacting the same sample suspected of containing the mecA nucleic acid with a third flap primer and a fourth flap primer having the formula:

5'-(X)$_n$Y'-3'  (II), wherein X represents the 5' portion of the flap primer that is non-complementary to the mecA nucleic acid and n=0 or 1, Y' represents the 3' portion of the flap primer that is complementary to the mecA nucleic acid, wherein X is about 3-30 nucleotides in length;

(c) incubating the mixture of step (a) and (b) under conditions sufficient to amplify the ldh1 and mecA nucleic acid, thereby generating an amplified ldh1 and mecA nucleic acids; and (d) detecting the amplified if present ldh1 and mecA nucleic acids.

The ldh1 and mecA nucleic acid can comprise the following sequences:

```
SEQ ID NO: 1:
                                         (SEQ ID NO: 1)
GGTGAACATGGTGACACTGAATTACCAGTATGGTCACACGCTAATATTGC

GGGTCAACCTTTGAAGACATTACTTGAACAACGTCCTGAGGGCAAAGCGC

SEQ ID NO: 2:
                                         (SEQ ID NO: 2)
GTGCGTTAATATTGCCATTATTTTCTAATGCGCTATAGATTGAAAGGATCT

GTACTGGGTTAATCAGTATTTCACCTTGTCCGTAACC
```

The amplification of the mecA and ldh1 nucleic acids can be continuously monitored and the relative concentrations can be determined in real time. In some embodiments, the amplified mecA and ldh1 nucleic acids are present in a 1:1 ratio. A difference in concentration indicates a mixed infection of *Staphylococcus aureus* with a coagulase-negative carrier of mecA, in the sample.

In one embodiment detection is performed with a first fluorescent generating probe specific to ldh1 and second fluorescent generating probe specific for mecA wherein the emission wavelengths are different. In some embodiments detection is performed with ldh1 and mecA specific labeled primers, which can be fluorescence-generating primers.

In some embodiments methods for detecting ldh1 and mecA nucleic acid in a sample with an internal control are provided.

In some embodiments methods for comparing relative quantities of ldh1 and mecA nucleic acids in a sample are provided.

In some embodiments methods for detecting ldh1 and mecA in addition to SCCmec integration site(s) or bridge regions are provided. Methods have been disclosed for detecting mecA integration sites upstream and downstream of the mecA gene. U.S. Pat. No. 6,156,507 discloses a method which comprises performing a reaction with a sample by using a nucleotide sequence of a chromosomal DNA surrounding an integrated site of a SCCmec in a chromosome of an MSSA or methicillin-resistant coagulase-negative staphylococci (MSC-NS), wherein said method makes use of an occurrence of a negative reaction when said sample contains a SCCmec integrated therein. U.S. Pat. No. 7,838,221 describes methods that use novel SCCmec right extremity junction (MREJ) sequences for the detection and/or identification of methicillin-resistant *Staphylococcus aureus* (MRSA).

In carrying out the present methods, the reaction mixture typically comprises two flap primers: a forward flap primer and a reverse flap primer. The forward flap primer and the reverse flap primer can be, but need not be, of equal lengths. In some embodiments flap primers are used where n=0 in one or more primers.

In one embodiment, the 5' sequence portion of the flap primer that is non-complementary to the SA or MRSA nucleic acid (X) is about 9-15 nucleotides in length, usually about 10-14 or about 11-13 nucleotides in length, and more usually about 12 nucleotides in length. The 5' sequence portion of the flap primer that is non-complementary to the SA or MRSA nucleic acid (X) can be 4, 5, 6, 7, 8, 9, 10, 11, 12, 13, 14, or 15 nucleotides in length.

In certain instances, the 3' sequence portion of the flap primers that are complementary to the SA or MRSA nucleic acid (Y) comprise a greater number of nucleotides than the 5' sequence portion of the flap primer that is non-complementary to the SA and MRSA nucleic acid (X). For example, the 3' sequence portion of the flap primer that is complementary to the SA or MRSA nucleic acid (Y) can comprise about 55%, 60%, 65%, 70%, 75%, 80%, 85%, or 90% of the total length of a flap primer.

In certain other instances, the 5' sequence portion of the flap primer that is non-complementary to the SA or MRSA nucleic acid (X) comprises about an equal number of nucleotides as the 3' sequence portion of the flap primer that is complementary to the SA or MRSA nucleic acid (Y). For example, the X and Y portions each can be about 4-30, 6-25, 8-20, or 10-15 nucleotides in length, usually about 10-14 or 11-13 nucleotides in length, and more usually about 12 nucleotides in length. The X and Y portions each can be 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In another embodiment, the 5' sequence portion of the flap primer that is non-complementary to the SA or mecA nucleic acid (X) comprises at least about 60%, 65%, 70%, 75%, 80%, 90%, or 95% adenine or thymine nucleotide bases, or modified bases thereof.

In some embodiments, the 5' sequence portion of the flap primer that is non-complementary to the ldh1 or mecA nucleic acid (X) comprises the following sequence: AATAAATCATAA (SEQ ID NO:3).

In some embodiments primers without flaps complementary to the ldh1 or mecA nucleic are provided for amplification. In some instances one flap primer and one primer without a flap are provided.

In other embodiments, the Y portion of the first flap primer comprises the following sequence: GGT*GA*ACA*TGGTGACACTG AAT-3' (SEQ ID No:4), wherein T* is 5-(4-hydroxy-but-1-ynyl)-1H-pyrimidine-2,4-dione (SUPER TCK, Elitech Group) and A* is 4-(4,6-Diamino-1H-pyrazolo[3,4-d]pyrimidin-3-yl)-but-3-yn-1-ol (SUPER A®, Elitech Group). In further embodiments, the Y portion of the second flap primer comprises the following sequence: GCGCTTTGCCCTCAGGACG-3' (SEQ ID NO:5). Preferably, the first flap primer comprises the following sequence: 5'-AATAA-ATCATAAGGT*GA*ACA*TGGTGACACTGAAT-3' (SEQ ID NO:6), wherein the underlined nucleotide sequence is non-complementary to the SA sequence and T* is SUPER T® and A® is SUPER A®; and the second flap primer comprises the following sequence: 5' AATAAAT-CATAAGCGCITGCCCTCAGGACG-3' (SEQ ID NO:7), wherein the underlined nucleotide sequence is non-complementary to the ldh1 sequence.

In other embodiments, the third flap mecA primer comprises the following sequence: GTGCGTTAATATTGCCAT-TATTTTCTAATGCG-3' (SEQ ID NO:8), wherein n=0. In further embodiments, the fourth flap mecA primer comprises the following sequence: GGTTACGGACAAGGT-GAAATAITGATTAACC-3' (SEQ ID NO:9), wherein n=0 and I is 3-alkynyl-1H-pyrazolo[3,4-d]pyrimidin-4(5H)-one (Super Inosine).

The sample is typically obtained from an animal suspected of having a SA/MRSA infection. Preferably, the animal is a human. Examples of samples suitable for use in the methods include, but are not limited to, a cerebrospinal fluid (CSF), a nasopharyngeal swab, a throat swab, wound or rectal swab, a stool sample, and a combination thereof.

ldh1 and mecA nucleic acids can be detected using any of the methods of detection known in the art. For example, detection can be carried out after completion of an amplification reaction (e.g., using ethidium bromide in an agarose gel) or simultaneously during an amplification reaction ("real-time detection"). See, e.g., PCR Primer: A Laboratory Manual, Dieffenbach et al. (eds.), Cold Spring Harbor Laboratory Press (2003); McPherson et al., *PCR Basics*, 2000; and *Rapid Cycle Real-time PCR Methods and Applications: Quantification*, Wittwer et al. (eds.), Springer-Verlag (2004). Preferably, the amplified SA and MRSA nucleic acids are detected by hybridization to a probe that specifically binds to the amplified SA or MRSA nucleic acid. In certain instances, the amplified ldh1 or mecA nucleic acid can be detected using one or more fluorescence-generating probes. Fluorescence-generating probes include probes that are cleaved to release fluorescence (e.g., Taqman, Centaurus, etc.), nucleic acid binding compounds (e.g., U.S. Pat. Nos. 5,994,056, 6,171,785, and 6,569,627; Bengtsson et al., *Nucl. Acids Res.*, 31: e45 (2003)), hybridization-based probes (e.g, MGB Eclipse, Molecular Beacons, Pleiades, Centaurus, etc.), and the like. In certain embodiments, the SA or MRSA nucleic acid is detected with one or more nucleic acid binding fluorescent compounds (e.g., SYBR® Green 1 (Molecular Probes; Eugene, Oreg.), BOXTOX, BEBO (TATAA Biocenter; Gotenborg, Sweden), etc.).

In one embodiment, the ldh1 or mecA nucleic acid is detected using a fluorescence-generating probe that hybridizes to either the ldh1 or mecA nucleic acids and one or more nucleotide bases of at least one flap primer sequence (typically, the complementary portion, Y). For example, the fluorescence-generating probe can hybridize to the SA nucleic acid and to one or more nucleotide bases of the forward flap primer sequence, one or more nucleotide bases of the reverse flap primer sequence, or simultaneously to one or more nucleotide bases of both the forward and the reverse flap primer sequences. The fluorescence-generating probe can optionally hybridize to the ldh1 or mecA nucleic acid and to 1, 2, 3, 4, 5, 6, 7, 8, 9, or 10 nucleotide bases of at least one flap primer sequence, particularly the complementary portion (Y) of a flap primer.

In a preferred embodiment, the fluorescence-generating probe for ldh1 gene comprises the following sequence:

(SEQ ID NO: 10)
5'-Ra-G*ACATTACT*T*GA*ACAA*CG-Rb-5', wherein Ra is independently selected from $(M)_a$-Fl and $(M)_a$-Q, Rb is independently selected from $(M)_a$-Fl and $(M)_a$-Q, and M is a minor groove binder, a is 0 or 1, Fl is a fluorophore with emission wavelength between about 400 and 900 nm, G* is 6-amino-1H-pyrazolo[3,4-d]pyrimidin-4(5H)-one (SUPER G®, Elitech Group) and Q is a non-fluorescent quencher, with the proviso that the substitution of Ra and Rb allows quenching of fluorescence when the probe is unhybridized.

In another preferred embodiment, the fluorescence-generating probe for mecA comprises the following sequence:

(SEQ ID NO: 11)
5'-Ra-G*AAAGGATCTGTACTGG*G --Rb-5, wherein Ra is independently selected from (M)$_a$-Fl and (M)$_a$-Q, Rb is independently selected from (M)$_a$-Fl and (M)$_a$-Q, and M is a minor groove binder, a is 0 or 1, Fl is a fluorophore with emission wavelength between about 400 and 900 nm, G* is SUPER G® (Elitech Group) and Q is a non-fluorescent quencher, with the proviso that the substitution of Ra and Rb allows quenching of fluorescence when the probe is unhybridized.

In one embodiment Ra in SEQ ID NO: 10 is (M)a-Fl wherein M is DPI$_3$, Fl is Aquaphlour™ 554 and Q is the Eclipse® Dark Quencher and SEQ ID NO:11 Ra in SEQ ID NO: 11 is (M)a-Fl wherein M is DPI$_3$, Fl is FAM and Q is the Eclipse® Dark.

The preferred primers can incorporate additional features, which allow for the detection or immobilization of the primer but do not alter the basic property of the primer, e.g., to act as a point of initiation of nuclei acid synthesis. In some instances, the primers contain one or more non-natural bases or modified bases in either or both the complementary and non-complementary sequence regions of the primer.

In certain instances, amplification is carried out using a polymerase. The polymerase can, but need not, have 5' nuclease activity. In certain other instances, primer extension is carried out using a reverse transcriptase and amplification is carried out using a polymerase.

In another embodiment, the primer sequences overlap, wherein the stability of the overlapping sequence duplex is less than that of the stability of the individual primer target duplexes.

In another aspect, methods are provided for simultaneously detecting nucleic acids from a plurality of *S. aureus* in a sample, comprising:
  (a) contacting a sample suspected of containing the *S. aureus* nucleic acids with:
    (i) a first flap primer comprising the following sequence: 5'-AATAAATCATAAGGT*GA*ACA*TGGTGA-CACTGAAT-3' (SEQ ID NO:6, wherein the underlined nucleotide sequence is non-complementary to the ldh1 sequence and A* is SuperA® and T* is Super T® modified bases; and
    (ii) a second flap primer comprising the following sequence: 5'-AATAAATCATAAGCGCTTTGC-CCTCAGGACG-3' (SEQ ID NO:7), wherein the underlined nucleotide sequence is non-complementary to the ldh1 sequence,
  (b) incubating the reaction mixture of step (a) under conditions sufficient to amplify the ldh1 nucleic acid, thereby generating amplified nucleic acids from a sample containing SA; and
  (c) detecting the amplified SA nucleic acids.

In the method for simultaneously detecting nucleic acids, an additional step after step (a) can be added contacting the sample after step (a) in which the mixture of step (a) is contacted with:
  (i) a third flap primer comprising a sequence of SEQ ID NO:8, GTGCGTTAATATTGCCATTATTTTCTAAT-GCG; and
  (ii) a fourth flap primer comprising a fourth sequence of SEQ ID NO:9, GGTTACGGACAAGGTGAAATAIT-GATTAACC, wherein I is 3-alkynyl-1H-pyrazolo[3,4-d]pyrimidin-4(5H)-one (Super Inosine), wherein the third and fourth flap primers each comprise a sequence portion that is complementary to the mecA nucleic acid.

In a preferred embodiment the primers and probes for the detection of mecA, ldh1 and internal control are multiplexed. Each of the probes is individually labeled with a different label. In another embodiment the probes have the same label.

The sample is typically obtained from an animal suspected of having a MRSA infection. Preferably, the animal is a human. Examples of samples suitable for use in the methods include, but are not limited to, a wound swab, a nasopharyngeal swab, a throat swab, a rectal swab, a stool sample, and a combination thereof.

In yet another aspect, kits are provided for detecting SA nucleic acid in a sample, comprising:
  (a) a first flap primer comprising the following sequence: 5'-AATAAATCATAAGGT*GA*ACA*TGGTGACACTG-AAT-3' (SEQ ID NO:6), wherein the underlined nucleotide sequence is non-complementary to the ldh1 sequence and A* is Super A and T* is Super T; and
  (b) a second flap primer comprising the following sequence: 5' AATAAATCATAAGCGCTTTGCCCTCAG-GACG-3' (SEQ ID NO:7), wherein the underlined nucleotide sequence is non-complementary to the ldh1 sequence.

In another aspect, kits are provided for detecting mecA nucleic acids in a sample, either alone or in combination with those for detecting ldh1 nucleic acids, comprising:
  (a) a first primer comprising the following sequence: 5'-GTGCGTTAATATTGCCATTTTTCTATTTCTAAT-GCG-3' (SEQ ID NO:8), and
  (b) a second primer comprising the following sequence: 5' GGTTACGGACAAGGTGAAATAITGATTAACC-3' (SEQ ID NO:9).

In certain instances, the kits further comprise a fluorescence-generating probe such as a hybridization-based fluorescent probe or a nucleic acid binding fluorescent compound. In a preferred embodiment, the ldh1 fluorescence-generating probe comprises the following sequence:

(SEQ ID NO: 10)
5'-Ra-G*ACATTACT*T*GA*ACAA*CG-Rb-5', wherein Ra is independently selected from (M)$_a$-Fl and (M)$_a$-Q. Rb is independently selected from (M)$_a$-Fl and (M)$_a$-Q, and M is a minor groove binder, a is 0 or 1, Fl is a fluorophore with emission wavelength between about 400 and 900 nm, G* is Super G® (Elitech Group) and Q is a non-fluorescent quencher, with the proviso that the substitution of Ra and Rb allows quenching of fluorescence when the probe is unhybridized.

In other instances, the kits further comprise a fluorescence-generating probe such as a hybridization-based fluorescent probe or a nucleic acid binding fluorescent compound.

In another preferred embodiment, the mecA fluorescence-generating probe comprises the following sequence:

(SEQ ID NO: 11)
5'-Ra-G*AAAGGATCTGTACTGG*G-Rb-3', wherein Ra is independently selected from (M)$_a$-Fl and (M)$_a$-Q, Rb is independently selected from (M)$_a$-Fl and (M)$_a$-Q, and M is a minor groove binder, a is 0 or 1, Fl is a fluorophore with emission wavelength between about 400 and 900 nm, G* is Super G® (Elitech Group) and Q is a non-fluorescent quencher, with the proviso that the substitution of Ra and Rb allows quenching of fluorescence when the probe is unhybridized.

In yet another instance the kits comprise ldh1 primer pair and mecA primer pair.

In some instances the kits comprise a ldh1 probe and a mecA probe.

In certain other instances, the kits further comprise a control nucleic acid that is suitable for use as an internal control. The IC template contains nonsense, non-specific target DNA fragment in a plasmid vector. Preferably, the plasmid insert of the control nucleic acid comprises the following sequence:

```
                                        (SEQ ID NO: 12)
5'-CTGCACGGACCAGTTACTTTACGGACCACGTACCGCATTGGTACA

AGATCTCCGGTAGAAAAAATGAG-3'.
```

The kits can also comprise primers and probes directed against the control nucleic acid. As a non-limiting example, a control probe (e.g., a fluorescence-generating probe) and a set of control primers designed against the nucleic acid sequence nonsense, non-specific target DNA fragment in a plasmid vector (SEQ ID NO:12) can be included in the kits. Preferably, the control probe and primers have the following sequences:

```
                        (SEQ ID NO: 13)
Probe:    5'-Ra-G*AATG*CGGTACGTGGTCC-Rb-3';

(SEQ ID NO: 14)
Primers:  CTGCACGGACCAGTTACTTTACG;

(SEQ ID NO: 15)
          CTCATTTTTTCTACCGGAGATCTTGT,
``` wherein Ra is independently selected from $(M)_a$-Fl and $(M)_a$-Q, Rb is independently selected from $(M)_a$-Fl and $(M)_a$-Q, and M is a minor groove binder, a is 0 or 1, Fl is a fluorophore with emission wavelength between about 400 and 900 nm, G* is Super G® (Elitech Group) and Q is a non-fluorescent quencher, with the proviso that the substitution of Ra and Rb allows quenching of fluorescence when the probe is unhybridized.

In further embodiments, a mutation in ldh1 and mecA genes can be detected in the following method:

(a) contacting the sample with a first flap primer and a second flap primer having the formula:

$$5'-(X)_n Y-3' \quad (I),$$

wherein X represents a 5' portion of the flap primers that is non-complementary to the ldh1 gene, n is 0 or 1, Y represents a 3' portion of the flap primers that is complementary to the ldh1 gene, and X is about 3-30 nucleotides in length;

(b) contacting the sample after step (a) with a third flap primer and a fourth flap primer having the formula:

$$5'-(X)_n Y'-3' \quad (I),$$

wherein X represents a 5' portion of the flap primers that is non-complementary to the mecA gene, n is 0 or 1, Y' represents a 3' portion of the flap primers that is complementary to the mecA gene, and X is about 3-30 nucleotides in length;

(c) incubating the sample following steps (a) and (b) under conditions sufficient to produce amplified ldh1 and mecA genes; and (d) contacting the amplified ldh1 and mecA genes with fluorescence-generating probes, wherein a first fluorescence-generating probe is complementary to the amplified ldh1 gene and a wild-type ldh1 gene and a second fluorescence-generating probe is complementary to the amplified mecA gene and a wild-type mecA gene, and (e) performing a melting curve analysis on the amplified ldh1 and mecA genes in the presence of the fluorescence-generating probes, wherein a difference of about 3-12° C. between a melting temperature ($T_m$) of the amplified and wild-type ldh1 nucleic acids indicates the presence of a mutation in the amplified ldh1 nucleic acid and a difference of about 3-12° C. between the melting temperature ($T_m$) of the amplified and wild-type mecA nucleic acids indicates the presence of a mutation in the amplified mecA nucleic acid.

The method can additionally include determining the mixed infection where ldh1 and mecA or $mecA_{LGA251}$ signals come from different organisms by comparing relative quantities of ldh1 and mecA or $mecA_{LGA251}$ markers. Equal quantities of ldh1 and mecA or ldh1 and $mecA_{LGA2511}$ suggest MRSA infection while different quantities suggest a MRSA-negative mixed infection of ldh1 and mecA carriers.

The present method allows the specific, sensitive, and rapid detection of SA and MRSA. MRSA infection is often not clinically distinguishable from other mecA carrying bacteria and other viral pathogens for which specific therapies are available. The present methods overcome this problem in diagnosis, by providing rapid specific detection of SA and MRSA, thereby eliminating false positive observed in some of the assays in the art. In addition, the hybridization-based probes allow melting curve analysis, which can identify potential new mutants of ldh1, mecA and $mecA_{LGA251}$.

In certain other instances, the kits further comprise a control nucleic acid that is suitable for use as a positive control (PC). The PC template contains portions of ldh1 and mecA DNA in a plasmid vector. Preferably, the plasmid insert of the control nucleic acid comprises the following sequence:

```
                                                 (SEQ ID NO: 18)
5'-ACGTAGCGTCGATGCTCAAATTATTGGTGAACATGGTGACACTGAA

TTACCAGTATGGTCACACGCTAATATTGCGGGTCAACCTTTGAAGACAT

TACTTGAACAACGTCCTGAGGGCAAAGCGCAAATTGAACAAATTTTTGT

TCAAACACGTGATGCAGCATATGACATTATTCAAGCTAAAGGTGCCACT

TATTATGGTGTTGCAATGGGATTAGCTAGAAAGCTATCTGCAGAATTCGC

CCTTTTACGACTTGTTGCATACCATCAGTTAATAGATTGATATTTTCTT

TGGAAATAATATTTTTCTTCCAAACTTTGTTTTTCGTGTCTTTTAATAA

GTGAGGTGCGTTAATATTGCCATTATTTTCTAATGCGCTATAGATTGAA

AGGATCTGTACTGGGTTAATCAGTATTTCACCTTGTCCGTAACCTGAAT

CAGCTAATAATATTTCATTATCTAAATTTTTGTTTGAAATTTGAGCATT

ATAAAATGGATAATCACTTGGTATATCTTCACCAACACCTAG-3'.
```

In certain other instances, the kits further comprise a control nucleic acid that is suitable for use as a $mecA_{LGA251}$ positive control ($mecA_{LGA251}$ PC). It contains a single fragment of LGA251 mecA gene in a plasmid vector. Preferably, the plasmid insert of the control nucleic acid comprises the following sequence:

(SEQ ID NO: 19)
CTCGTCAGAATTAATTGGACCCACATAACCTAAAAGGTGTACTGT

TGCTTCGTTCAATGGATAAACACGGC

In other embodiments primers without flaps complementary to mecA$_{LGA251}$ are provided for amplification. In some instances both primers are without flaps. In other instances one primer without a flap and one flap primer are provided.

In some embodiments the first mecA$_{LGA251}$ primer comprises the following sequence: CTCGTCAGAAT*T*AATTGGACCCAC (SEQ ID NO:20), wherein T* is 5-(4-hydroxy-but-1-ynyl)-1H-pyrimidine-2,4-dione (SUPER T®, Elitech Group). In further embodiments the second mecA$_{LGA251}$ primer comprises the following sequence: GCCGTGTTTACCATITAAC-GAAGCA (SEQ ID NO:21).

In other embodiments amplification of the mecA$_{LGA251}$ gene is performed with primer pairs comprising the sequences GGATATGGCCAAGGCGAGATACTAG-TAAACC (SEQ ID NO:23) and GAGGATTTTGTAT-ATTTCCGTTATTTTCTAAAGCACTG (SEQ ID NO:24); AATAAATCATAAGGGTTGAACCTGGTGATGTAGTG (SEQ ID NO:25) and AATAAATCATAACAATAAAAAAGAGCCT*T*T*GCT-CAAC (SEQ ID NO:26). In another method comprises any 10 nucleotide bases of SEQ ID NO:23 to 26.

In a preferred embodiment, the fluorescence-generating probe for mecA$_{LGA251}$ gene comprises the following sequence:

(SEQ ID NO: 27)
5'-Ra-G*TAAAAGGTGTA*CTGTTGC-Rb-3' wherein Ra is independently selected from (M)$_a$-Fl and (M)$_a$-Q, Rb is independently selected from (M)$_a$-Fl and (M)$_a$-Q, G* is 6-amino-1H-pyrazolo[3,4-d]pyrimidin-4 (5H)-one (SUPER G®, Elitech Group) and M is a minor groove binder, a is 0 or 1, Fl is a fluorophore with emission wavelength between about 400 and 900 nm, and Q is a non-fluorescent quencher, with the proviso that the substitution of Ra and Rb allows quenching of fluorescence when the probe is unhybridized.

In another preferred embodiment, the fluorescence-generating probe for mecA$_{LGA251}$ comprises the following sequences:

(SEQ ID NO: 28)
5'-Ra-G*ATAAAAT*T*T*GTA*TA*GG-Rb-3'
and (SEQ ID NO: 29)
5'-Ra-FAM-AAAT*T*T*CAAATCACTAC-Rb-3' wherein Ra is independently selected from (M)$_a$-Fl and (M)$_a$-Q, Rb is independently selected from (M)$_a$-Fl and (M)$_a$-Q, and M is a minor groove binder, a is 0 or 1, Fl is a fluorophore with emission wavelength between about 400 and 900 nm, G* is 6-amino-1H-pyrazolo[3,4-d]pyrimidin-4(5H)-one (SUPER G®, Elitech Group), T* is Super T, A* is 4-(4,6-Diamino-1H-pyrazolo[3,4-d]pyrimidin-3-yl)-but-3-yn-1-ol (SUPER A®, Elitech Group) and Q is a non-fluorescent quencher, with the proviso that the substitution of Ra and Rb allows quenching of fluorescence when the probe is unhybridized. In another method comprises any 10 nucleotide bases of SEQ ID No: 27 to 29.

IV. Primers and Probes

In one aspect, oligonucleotide primers ("overhang primers," "flap primers," or "adapter primers") are provided which are most generally noted as 5'-X—Y-3' or 5'-(X)$_n$Y'-3' primers. X represents the sequence portion of the primer that is non-complementary to the ldh1 or mecA nucleic acid, and Y or Y' represents the sequence portion of the primer that is complementary to the ldh1 or mecA nucleic acid, respectively.

Accordingly, in one group of embodiments, the primer has the formula:

$$5'\text{-}(X)_n\text{—}Y\text{-}3' \quad \quad (I)$$

or $$5'\text{-}(X)_nY'\text{-}3' \quad \quad (II),$$

wherein X represents the 5' sequence of the primer non-complementary to the ldh1 or mecA nucleic acid, Y represents the complementary 3' sequence of the primer to ldh1, Y' represents the complementary 3' sequence of the primer to mecA, and 5'-X—Y-3' or 5'-(X)$_n$Y'-3' represents the nucleic acid oligomer primer. In certain further embodiments, X is [A-B]$_m$ and Y is [A-B]$_p$, wherein A represents a sugar phosphate backbone, modified sugar phosphate backbone, locked nucleic acid backbone, a chimera or a variant thereof used in nucleic acid preparation; B represents a nucleic acid base or a modified base of a base; and the subscript m is an integer of from about 3-18 or 4-16, usually from about 8-15, 10-14, or 11-13, and more usually about 12. The subscript p is an integer of from about 4-50, usually from about 8-20, 10-18, or 12-16. In certain embodiments, the values of the subscripts m and n are equal, for example, both m and p simultaneously can be an integer of from about 8-15, 10-14 or 11-13, and more usually about 12.

The primers and probes are generally prepared using solid phase methods known to those of skill in the art. In general, the starting materials are commercially available, or can be prepared in a straightforward manner from commercially available starting materials using suitable functional group manipulations as described in, for example, March et al., ADVANCED ORGANIC CHEMISTRY—Reactions, Mechanisms and Structures, 4th ed., John Wiley & Sons, New York, N.Y. (1992).

In one embodiment, the primers and probes can comprise any naturally occurring nucleotides, non-naturally occurring nucleotides, or modified nucleotides known in the art (see, e.g., U.S. Patent Publication No. 20050118623; and U.S. Pat. No. 6,949,367).

In one embodiment, the primers and probes can comprise universal or promiscuous bases.

Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in co-owned RE 38,416; U.S. Patent Publication No. 20050118623, and U.S. Pat. No. 6,127,121). Included in the modified bases are those that differ from naturally-occurring bases where the sugar backbone is modified (EP Patent No.

1314734), universal bases (PCT Patent Publication No. WO 02/062816) and promiscuous bases (U.S. Pat. No. 7,348, 146).

Exemplary modified bases include, but are not limited to, the guanine analogue 6-amino-1H-pyrazolo[3,4-d]pyrimidin-4(5H)-one (ppG or PPG, also referred to as SUPER G®) and the adenine analogue 4-amino-1H-pyrazolo[3,4-d]pyrimidine (ppA or PPA). The xanthene analogue 1H-pyrazolo[5,4-d]pyrimidin-4(5H)-6(7H)-dione (ppX) can also be used. These base analogues, when present in an oligonucleotide, strengthen hybridization and improve mismatch discrimination. All tautomeric forms of naturally-occurring bases, modified bases, and base analogs may be included in the oligonucleotide conjugates. Other modified bases useful in the present methods include 6-amino-3-prop-1-ynyl-5-hydropyrazolo[3,4-d]pyrimidine-4-one (PPPG); 6-amino-3-(3-hydroxyprop-1-yny)1-5-hydropyrazolo[3,4-d]pyrimidine-4-one (HOPPPG); 6-amino-3-(3-aminoprop-1-ynyl)-5-hydropyrazolo[3,4-d]pyrimidine-4-one ($NH_2$PPPG); 4-amino-3-(prop-1-ynyl)pyrazolo[3,4-d]pyrimidine (PPA); 4-amino-3-(3-hydroxyprop-1-ynyl)pyrazolo[3,4-d]pyrimidine (HOPPPA); 4-amino-3-(3-aminoprop-1-ynyl)pyrazolo[3,4-d]pyrimidine ($NH_2$PPPA); 3-prop-1-ynylpyrazolo[3,4-d]pyrimidine-4,6-diamino (($NH_2$)2PPPA); 2-(4,6-diaminopyrazolo[3,4-d]pyrimidin-3-yl)ethyn-1-ol (($NH_2$) 2PPPAOH); 3-(2-aminoethynyl)pyrazolo[3,4-d]pyrimidine-4,6-diamine (($NH_2$)2PPPAN$H_2$); 5-prop-1-ynyl-1,3-dihydropyrimidine-2,4-dione (PU); 5-(3-hydroxyprop-1-ynyl)-1,3-dihydropyrimidine-2,4-dione (HOPU); 6-amino-5-prop-1-ynyl-3-dihydropyrimidine-2-one (PC); 6-amino-5-(3-hydroxyprop-1-yny)-1,3-dihydropyrimidine-2-one (HOPC); 6-amino-5-(3-aminoprop-1-yny)-1,3-dihydropyrimidine-2-one ($NH_2$PC); 5-[4-amino-3-(3-methoxyprop-1-ynyl)pyrazol[3,4-d]pyrimidinyl]-2-(hydroxymethyl)oxolan-3-ol ($CH_3$OPPPA); 6-amino-1-[4-hydroxy-5-(hydroxymethyl)oxolan-2-yl]-3-(3-methoxyprop-1-ynyl)-5-hydropyrazolo[3,4-d]pyrimidin-4-one, ($CH_3$OPPPG); 4, (4,6-Diamino-1H-pyrazolo[3,4-d]pyrimidin-3-yl)-but-3-yn-1-ol (SUPER A®); 6-amino-3-(4-hydroxy-but-1-ynyl)-1,5-dihydro-pyrazolo[3,4-d]pyrimidin-4-one; 5-(4-hydroxy-but-1-ynyl)-1H-pyrimidine-2,4-dione (SUPER T®); 3-iodo-1H-pyrazolo[3,4-d]pyrimidine-4,6-diamine (($NH_2$)$_2$PPAI); 3-bromo-1H-pyrazolo[3,4-d]pyrimidine-4,6-diamine (($NH_2$)2PPABr); 3-chloro-1H-pyrazolo[3,4-d]pyrimidine-4,6-diamine (($NH_2$)2PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-choro-1H-pyrazolo[3,4-d]pyrimidin-4-ylamine (PPACI).

In addition to the modified bases noted above, the oligonucleotides can have a backbone of sugar or glycosidic moieties, preferably 2-deoxyribofuranosides wherein all internucleotide linkages are the naturally-occurring phosphodiester linkages. In alternative embodiments, however, the 2-deoxy-3-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_2$-6 alkenyl group (2-(O—$C_{26}$ alkenyl) ribose), or is replaced by a fluoro group (2-fluororibose). Related useful oligomer-forming sugars are those that are "locked," i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides, and 2',3'-dideoxy-3'-aminoribofuranosides. Oligonucleotides containing α-D-arabinofuranosides can be prepared as described in U.S. Pat. No. 5,177, 196. Oligonucleotides containing 2',3'-dideoxy-3'-aminoribofuranosides are described in Chen et al., *Nucleic Acids Res.*, 23:2661-2668 (1995). Synthetic procedures for locked nucleic acids (Singh et al., *Chem. Comm.*, 455-456 (1998); Wengel, *Ace. Chem. Res.*, 32:301-310 (1998)) and oligonucleotides containing 2'-halogen-2'-deoxyribofuranosides (Palissa et al., *Z. Chem.*, 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., *Nucl. Acids Res.*, 23:2662-2668 (1995)). Combinations of oligonucleotide linkages are also within the scope of this disclosure. Still other backbone modifications are known to those of skill in the art.

The ability to design probes and primers in a predictable manner using an algorithm that can direct the use or incorporation of modified bases, minor groove binders, fluorphores, and/or quenchers based on their thermodynamic properties have been described in, e.g., U.S. Pat. No. 6,683, 173. Accordingly, the use of any combination of normal bases, unsubstituted pyrazolo[3,4-d]pyrimidine bases (e.g., PPG and PPA), 3-substituted pyrazolo[3,4-d]pyrimidines, modified purines, modified pyrimidines, 5-substituted pyrimidines, universal bases, sugar modifications, backbone modifications, and/or minor groove binders to balance the $T_m$ (e.g., within about 5-8° C.) of a hybridized product with a modified nucleic acid is contemplated by the present disclosure.

Since the FRET probes of the present methods are not cleaved, in contrast to 5'-nuclease-based assays that are, melting curve analysis can be used to analyze mutations that may occur in the probe region. Analysis of mutations under the probe have been reported (Stevenson J et al., J Clin Microbiol., 43: 2391-8 (2005)).

Also provided are oligomer microarrays wherein at least one of the oligomers described herein is present on the array. Oligomers disclosed herein can be used as immobilized oligomers in oligomer arrays such as those described in, for example, U.S. Pat. Nos. 5,492,806; 5,525,464; 5,556,752 and PCT publications WO 92/10588 and WO 96/17957.

Detailed descriptions of the chemistry used to synthesize oligonucleotides by the phosphoramidite method are provided in U.S. Pat. Nos. 4,458,066 and 4,415,732; Caruthers et al., *Genetic Engineering*, 4:1-17 (1982); and Users Manual Model 392 and 394 Polynucleotide Synthesizers, pages 6-1 through 6-22, Applied Biosystems, Part No. 901237 (1991). Labeled oligonucleotides can be synthesized enzymatically, e.g., using a DNA polymerase or ligase, (see, e.g., Stryer, Biochemistry, Chapter 24, W. H. Freeman and Company (1981)), or by chemical synthesis, e.g., by a phosphoramidite method, a phosphite-triester method, and the like, (see, e.g., Gait, OLIGONUCLEOTIDE SYNTHESIS, IRL Press (1990)). Labels can be introduced during enzymatic synthesis utilizing labeled nucleoside triphosphate monomers, or introduced during chemical synthesis using labeled non-nucleotide or nucleotide phosphoramidites, or may be introduced subsequent to synthesis.

V. Additional Amplification Reaction Components

Buffers

Buffers that may be employed are borate, phosphate, carbonate, barbital, Tris, etc., based buffers (see, e.g., U.S. Pat. No. 5,508,178). The pH of the reaction should be maintained in the range of from about 4.5 to about 9.5 (see, e.g., U.S. Pat. No. 5,508,178). The standard buffer used in amplification reactions is a Tris based buffer between 10 and 50 mM with a pH of around 8.3 to 8.8 (see, e.g., Innis et al., supra).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

Salt Concentration

The concentration of salt present in the reaction can affect the ability of primers to anneal to the target nucleic acid (see, e.g., Innis et al., supra). Potassium chloride can be added up to a concentration of about 50 mM to the reaction mixture to promote primer annealing. Sodium chloride can also be added to promote primer annealing (see, e.g., Innis et al., supra).

Magnesium Ion Concentration

The concentration of magnesium ion in the reaction can affect amplification of the target SA or MRSA nucleic acid sequence (see, e.g., Innis et al., supra). Primer annealing, strand denaturation, amplification specificity, primer-dimer formation, and enzyme activity are all examples of parameters that are affected by magnesium concentration (see, e.g., Innis et al., supra). Amplification reactions should contain about a 0.5 to 6.0 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target SA or MRSA nucleic acid and the primers being used, among other parameters.

Deoxynucleotide Triphosphate Concentration

Deoxynucleotide triphosphates (dNTPs) are added to the reaction to a final concentration of from about 20 µM to about 300 µM. Typically, each of the four dNTPs (G, A, C, T) are present at equivalent concentrations (see, e.g., Innis et al., supra). In some embodiments, uracil N-glycosylase is used with dUTP (instead of TTP) in PCR reactions.

Nucleic Acid Polymerases

A variety of DNA dependent polymerases are commercially available that will function using the present methods and compositions. For example, Taq DNA Polymerase may be used to amplify target DNA sequences. The PCR assay may be carried out using as an enzyme component, a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases and Tfi DNA Polymerase marketed by Life Technologies, Promega or Pharmacia. Other examples of thermostable DNA polymerases that could be used include DNA polymerases obtained from, e.g., *Thermus* and *Pyrococcus* species. Concentration ranges of the polymerase may range from 1-5 units per reaction mixture. The reaction mixture is typically between about 5 µL and about 100 µL.

VI. Other Reagents

Additional agents are sometimes added to the reaction to achieve the desired results. For example, DMSO can be added to the reaction, but is reported to inhibit the activity of Taq DNA Polymerase. Nevertheless. DMSO has been recommended for the amplification of multiple target sequences in the same reaction (see, e.g., Innis et al., supra). Stabilizing agents such as glycerol, gelatin, bovine serum albumin, and non-ionic detergents (e.g., Tween-20) are commonly added to amplification reactions (see, e.g., Innis et al., supra). RNase Inhibitor (Ambion; Austin, Tex.) can also be added to limit RNA degradation. Additionally, betaine (Sigma-Aldrich; St. Louis, Mo.), an isostabilizing agent, can be added to equalize the contribution of GC- and AT-base pairing to the stability of the nucleic acid duplex.

VII. Minor Groove Binders

Minor groove binder oligonucleotide conjugates (or "probes") are described in, e.g., U.S. Pat. Nos. 5,801,155 and 6,312,894. These conjugates form hyper-stabilized duplexes with complementary DNA. In particular, sequence specificity of short minor groove binder probes is excellent for high temperature applications such as PCR. The probes/conjugates will also optionally have a covalently attached minor groove binder. A variety of suitable minor groove binders have been described in the literature (see, e.g., U.S. Pat. No. 5,801,155; Wemmer et al., *Curr. Opin. Struct. Biol.,* 7:355-361 (1997); Walker et al., *Biopolymers,* 44:323-334 (1997); Zimmer et al., *U. Prog. Biophys. Molec. Bio.,* 47:31-112 (1986); and Reddy et al., J. W., *Pharmacol. Therap.,* 84:1-111 (1999)).

The minor groove binder-quencher-oligonucleotide-fluorophore conjugates can be in a linear arrangement (as suggested by the formula 5'-M-Q-ODN-Fl-3' or 5'-M-Fl-ODN-Q-3') or in a branched arrangement wherein the quencher (Q) and the minor groove binder (M) are attached to a linking group that serves to join ODN, Q, and M. Additionally, the quencher can be attached at the distal (relative to attachment to ODN) terminus of the minor groove binder (e.g., 5'-Q-M-ODN-Fl-3'). Each of the arrangements is meant to be included when the linear abbreviation (M-Q-ODN-Fl) is used. Additionally, the minor groove binder and quencher portions each can be attached at either the 3' or 5' end of the oligonucleotide, or an internal position of the oligonucleotide, so long as such attachment does not interfere with the quenching mechanisms of the conjugate. Generally, this can be accomplished through the use of a suitable linking group (see, e.g., U.S. Pat. No. 7,381,818).

Suitable methods for attaching minor groove binders (as well as reporter groups such as fluorophores and quenchers described below) through linkers to oligonucleotides are described in, for example, U.S. Pat. Nos. 5,512,677; 5,419, 966; 5,696,251; 5,585,481; 5,942,610; and 5,736,626.

The minor groove binder is generally attached to the 3' or 5' position of the oligonucleotide portion via a suitable linking group. Attachment at the 5' end provides both a benefit of hybrid stability, since melting of an oligonucleotide duplex begins at the termini, but also reduces and/or prevents nuclease digestion of the probe during amplification reactions.

The location of a minor groove binder within a minor groove binder-oligonucleotide conjugate can also affect the discriminatory properties of such a conjugate. An unpaired region within a duplex will result in changes in the shape of the minor groove in the vicinity of the mispaired base(s). Since minor groove binders fit best within the minor groove of a perfectly-matched DNA duplex, mismatches resulting in shape changes in the minor groove would reduce binding strength of a minor groove binder to a region containing a mismatch. Hence, the ability of a minor groove binder to stabilize such a hybrid would be decreased, thereby increasing the ability of a minor groove binder oligonucleotide conjugate to discriminate a mismatch from a perfectly matched duplex. On the other hand, if a mismatch lies outside of the region complementary to a minor groove binder oligonucleotide conjugate, discriminatory ability for unconjugated and minor groove binder-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of minor groove binder oligonucleotide conjugates in this context lies in the fact that much shorter oligonucleotides compared to those used in the prior art (i.e., 20 mers or shorter), having greater discriminatory powers, can be used, due to the pronounced stabilizing effect of minor groove binder conjugation.

In one group of embodiments, the minor groove binder is selected from the group consisting of analogs of CC1065, lexitropsins, distamycin, netropsin, berenil, duocarmycin, pentamidine, and 4,6-diamino-2-phenylindole and pyrrolo[2.1 c][1,4]benzodiazepines.

Further preferred minor groove binders are those selected from the formulae:

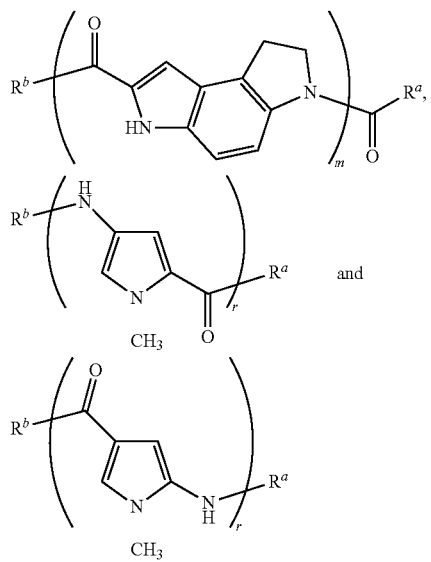

wherein the subscript m is an integer of from 2 to 5; the subscript r is an integer of from 2 to 10; and each $R^a$ and $R^b$ is independently a linking group to the oligonucleotide (either directly or indirectly through a quencher), H, —$OR^c$, —$NR^cR^d$, —$COOR^c$ or —$CONR^cR^d$, wherein each $R^c$ and $R^d$ is selected from H, ($C_2$-$C_{12}$)heteroalkyl, ($C_3$-$C_{12}$)heteroalkenyl, ($C_3$-$C_{12}$)heteroalkynyl, ($C_1$-$C_{12}$)alkyl, ($C_2$-$C_{12}$) alkenyl, ($C_2$-$C_{12}$)alkynyl, aryl($C_1$-$C_{12}$)alkyl and aryl, with the proviso that one of $R^a$ and $R^b$ represents a linking group to ODN or Q. In an additional embodiment, each of the rings in each structure can contain one or more additional substitutions selected from H, halogen, ($C_1$-$C_8$)alkyl, $OR_g$, $N(R_g)_2$, $N^+(R_g)_3$, $SR_g$, $COR_g$, $CO_2R_g$, $CON(R_g)_2$, $PO_3^=$ $(CH_2)_mSO_3^-$, $(CH_2)_mCO_2^-$, $(CH_2)_mOPO_3^{-2}$, and NHC(O) $(CH_2)_mCO_2$, and esters and salts thereof, wherein each $R_g$ is independently H or ($C_1$-$C_8$)alkyl, and the subscript m is an integer of from 0 to 6. The symbol $R_h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences.

Particularly preferred minor groove binders include the trimer of 3-carbamoyl-1,2-dihydro-(3H)-pyrrolo[3,2-e]indole-7-carboxylate ($CDPI_3$) or a substituted dihydrocyclopyrroloindole triamide ($DPI_3$), the pentamer of N-methylpyrrole-4-carbox-2-amide ($MPC_5$), and other minor groove binders that exhibit increased mismatch discrimination. Additional minor groove binder moieties that will find use are disclosed in U.S. Pat. No. 5,801,155. In certain embodiments, the minor groove binders can have attached water solubility-enhancing groups (e.g., sugars, amino acids, carboxylic acid or sulfonic acid substituents, and the like). See, e.g., RE 38,416; and U.S. Pat. No. 7,582,739.

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance (Ro) is described as the distance between the donor and acceptor molecules where the energy transfer is 50% efficient. Other mechanisms of fluorescence quenching are also known, such as collision and charge transfer quenching. There is extensive guidance in the art for selecting quencher and fluorophore pairs and their attachment to oligonucleotides (see, e.g., Haugland, HANDBOOK OF FLUORESCENT PROBES AND RESEARCH CHEMICALS, Ninth Edition, Molecular Probes, Eugene, Oreg. (2002) and the Web Edition at www.probes.com/handbook; and U.S. Pat. Nos. 3,996,345 and 4,351,760). Preferred quenchers are described in U.S. Pat. No. 6,727,356 and U.S. Pat. No. 6,790,945; and U.S. Patent Publication Nos. 20030096254 and 20020155484. Additional mono- and bis-azo dyes are commercially available from Berry and Associates (Dexter, Mich.) and Glen Research (Sterling, Va.).

Fluorophores useful in the present methods are generally fluorescent organic dyes that have been derivatized for attachment to the terminal 3' or 5' carbon of the oligonucleotide probe, preferably via a linking group. One of skill in the art will appreciate that suitable fluorophores are selected in combination with a quencher that is typically also an organic dye, which may or may not be fluorescent.

There is a great deal of practical guidance available in the literature for selecting appropriate fluorophore-quencher pairs for particular probes. See, for example, Pesce et al. (eds.), FLUORESCENCE SPECTROSCOPY, Marcel Dekker, New York (1971); White et al., FLUORESCENCE ANALYSIS: A PRACTICAL APPROACH, Marcel Dekker, New York (1970) and the like. The literature also includes references providing exhaustive lists of fluorescent and chromogenic (quenching) molecules and their relevant optical properties for choosing fluorophore-quencher pairs. See, e.g., Berlman, HANDBOOK OF FLUORESCENCE SPECTRA OF AROMATIC MOLECULES, 2ND EDITION, Academic Press, New York (1971); Griffiths, COLOUR AND CONSTITUTION OF ORGANIC MOLECULES, Academic Press, New York (1976); Bishop (ed.), INDICATORS, Pergamon Press, Oxford (1972); Haugland, HANDBOOK OF FLUORESCENT PROBES AND RESEARCH CHEMICALS, Ninth Edition, Molecular Probes, Eugene, Oreg. (2002) and the Web Edition at www.probes.com/handbook; Pringsheim, FLUORESCENCE AND PHOSPHORESCENCE, Interscience Publishers, New York (1949); and the like. Additionally, methods for derivatizing fluorophores and quenchers for covalent attachment via common reactive groups are well known. See, for example, Haugland, supra; and U.S. Pat. Nos. 3,996,345 and 4,351,760.

Preferred fluorophores are those based on xanthene dyes, a variety of which are available commercially with substituents useful for attachment of either a linking group or for direct attachment to an oligonucleotide. Another group of fluorescent compounds are the naphthylamines, having an amino group in the α- or β-position. Included among such naphthylamino compounds are 1-dimethylaminonaphthyl-5-sulfonate, 1-anilino-8-naphthalene sulfonate, and 2-p-toluidinyl-6-naphthalene sulfonate. Other dyes include 3-phenyl-7-isocyanatocoumarin, acridines such as 9-isothiocyanatoacridine and acridine orange, N-(p-(2-benzoxazolyl)phenyl)maleimide, benzoxadiazoles, stilbenes, pyrenes, and the like. Still other suitable fluorophores include the resorufin dyes, rhodamine dyes, cyanine dyes, and BODIPY dyes. Particularly preferred are phosphonylated dyes described in U.S. Pat. Nos. 7,671,218 and 7,767,834. Examples of suitable phosphonylated dyes are set forth in Table 1.

TABLE 1

| # | Name | Dye Structure |
|---|------|---------------|
| 1 | FAM | |
| 2 | AquaPhlour® 554 (AP 554) | |
| 3 | AquaPhlour® 593 (AP 593) | |
| 4 | AquaPhlour® 642 (AP 642) | |

Xanthene and Cyanine Dyes

VIII. Linking Groups

A variety of linking groups and methods are known to those of skill in the art for attaching fluorophores, quenchers, and minor groove binders to the 5' or 3' termini of oligonucleotides. See, for example, Eckstein, (ed.), OLIGONUCLEOTIDES AND ANALOGUES: A PRACTICAL APPROACH, IRL Press, Oxford (1991); Zuckerman et al., *Nuc. Acids Res.*, 15:5305-5321 (1987); Sharma et al., *Nuc. Acids Res.*, 19:3019 (1991); Giusti et al., *PCR Methods and Applications*, 2:223-227 (1993), U.S. Pat. Nos. 4,757,141 and 4,739,044; Agrawal et al., *Tetrahedron Letters*, 31:1543-1546 (1990); Sproat et al., *Nuc. Acids Res.*, 15:4837 (1987); Nelson et al., *Nuc. Acids Res.*, 17:7187-7194 (1989); and the like. Still other commercially available linking groups can be used that can be attached to an oligonucleotide during synthesis and are available from, e.g., Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, e.g., U.S. Pat. Nos. 5,231,191; 4,997,928; 6,653,473; 6,790,945; and 6,972,339; and PCT Patent Publication No. WO 01/42505.

IX. Methods of Use

The primers and probes to detect both MRSA and SA, based on a combined detection of ldh1 and mecA markers, provide numerous advantages over existing assay primers and probes, including specificity. The primers and probes are particularly useful when used to detect a target sequence in real-time (or coincident) with an amplification process such as, for example, PCR. Additionally, the preferred probes are not digested by 5'-nuclease activity. Accordingly, the amplification reactions can be archived and reevaluated by melting curve analysis.

The methods disclosed herein are practiced with deoxyribonucleic acid (DNA) as a starting material. Typically, the DNA target is amplified with any DNA-based amplification method. One such amplification method is the polymerase chain reaction (see, e.g., U.S. Pat. Nos. 4,683,195 and 4,965,188; and Mullis et al., *Cold Spring Harb. Symp. Quant. Biol.*, 51 Pt 1:263-273 (1986)). In some instances, the transcribed cDNA is amplified by methods other than PCR. The use of any one of the primers and probes in non-PCR amplification methods fall within the scope of this disclosure. In addition to the more traditional amplification reactions discussed above, the present methods are useful in amplifications involving three-way junctures (see, e.g., PCI Patent Publication No. WO 99/37085), signal amplification (see, e.g., Capadi et al., *Nuc. Acids Res.*, 28:E21 (2000)), RNase H, Rolling Circles, invasive cleavage of oligonucleotide probes by flap endonucleases (see, e.g., Lyamichev et al., *Nature Biotechnol.*, 17:292-296 (1999)), self-sustained sequence replication type assays (see, e.g., Mueller et al., *Histochem. Cell Biol.*, 108:431-437 (1997)), and the like.

Amplified DNA or cDNA is detected by conventional techniques that include the use of suitably labeled primers or probes. Suitable detectable labels include fluorescent, chemiluminescent, colorimetric, radioactive, chemical, antibodies and antigens, biotin, and the like. Suitable methods for detecting such labels are well known in the art and are commercially available.

The preferred probes are hybridization-based probes, which contain a minor groove binder group at the 5'-end of the probe. The use of these detection probes to detect amplified targets is described in U.S. Pat. Nos. 7,205,105 and 7,381,818. Alternatively, probes cleaved by the 5'-nuclease activity of polymerase are included within the scope of this disclosure (see, e.g., U.S. Pat. No. 6,312,894; and Livak, *Genet Anal.*, 14:143-149, 1999).

X. Kits

Kits are further provided for the detection of MRSA/SA nucleic acids (e.g., in a sample such as a biological sample). The kits typically comprise two or more components necessary for amplifying ldh1 and mecA nucleic acids. Components may be compounds, reagents, containers, and/or equipment. For example, one container within a kit may contain a first flap primer and a second flap primer, e.g. SEQ ID NOS: 6 and 7 and another container within a kit may contain a third and fourth flap primers, e.g., SEQ ID NO:9. In addition, kits may contain one or more probes, e.g., SEQ ID NO:10 and 11. The kits may also contain one or more control nucleic acid sequences, e.g., SEQ ID NO: 12, and probes and primers for amplifying the control sequence, e.g., SEQ ID NOS: 13, 14, and 15. In some embodiments, the kits comprise instructions for use, i.e., instructions for using the primers in amplification and/or detection reactions as described herein and comparing.

XI. Computer Analysis

In another embodiment, a method and system are provided for analyzing a subject's assay results to determine whether said subject is MRSA positive. Said system comprises: computer processor means for receiving, processing and communicating data; storage means for storing data including a reference database which includes mecA and ldh1 and control cycle thresholds (Cts) corresponding to their assigned MRSA detection status, namely MRSA positive, MRSA-negative/SA-negative, invalid analysis, MRSA-negative/SA-positive and MRSA-negative/SA-negative; and a computer program embedded within the computer processor. Cycle thresholds are defined as the number of cycles required for the fluorescent signal to cross the threshold, or exceed background level. Once data consisting of or including the result of a sample analysis, which includes measurements of mecA and ldh1 and control cycle thresholds (Cts) for a particular sample, is received or input, the computer program processes said data in the context of said reference database to determine, as an outcome, the subject's MRSA status. The outcome is communicable once known, preferably to a user having input said data.

In one embodiment the outcome is communicable to a medical provider.

In an additional embodiment where the reported result is "MRSA/SA Positive," this result is presumed positive for MRSA and comprises the detection of the mecA and ldh1 targets in approximately same quantities. MRSA positive is understood to include all mecA strains, including for example, $LGA_{251}$.

In an embodiment where the reported result is "MRSA Negative, SA Positive," this result is presumed positive for SA and comprises the detection of only the ldh1 target or detection of mecA and ldh1 in different quantities.

In an embodiment where the reported result is "MRSA/SA Negative," this result is presumed negative for SA and comprises the absence of detection of the ldh1 target.

In one embodiment where the reported result is "MRSA Positive," this result is presumed positive for MRSA and comprises the detection of a mecA junction sequence.

In one embodiment where the reported result is "MIRSA Negative," this result is presumed negative for MRSA and comprises the absence of detection of a mecA junction sequence.

In one embodiment where the reported result is "SA positive," this result is presumed positive for SA and comprises the detection of one or more SA sequence-specific targets with the proviso that the ldh1 target is also detected. Sequence specific ldh1 targets have been reported including a gap regulator gene region (see U.S. Pat. No. 6,946,267), as well as spa, nuc, Sa442, clfA, femA and femB.

In one preferred embodiment the result interpretation is performed by computer processing. In another preferred embodiment the computer processing is performed by an "if" excel function. The use of an "if" excel function computing a result interpretation is demonstrated in Example 8.

EXAMPLES

The following examples are provided to illustrate, but not to limit, the subject matter described herein.

PCR is performed using the final concentrations of the assay components in the mono-reagent shown in Table 2 below. dT(s)-AP593 is a passive reference control. 2×Tfi PCR Master Mix (Life Science Technologies, Inc) contains all the reagents necessary to perform PCR including uracil-N-glycosylase (UNG). The enhancer is 2.65% glycerol and 0.3% Triton X-100.

Twenty microliters of the mono-reagent are introduced in a 96 well PCR plate with 10 µL of sample nucleic acid. Sample nucleic acid is obtained by extraction with easy-MAG using NucliSENSE easyMAG extraction reagents and instructions (Biomieurex, l'Etoile, France). The plate is sealed with MicroAmp® Optical Adhesive Film (Applied Biosystems, Foster City, Calif.) and then centrifuged to collect the assay solution in the bottom of the plate well. The assay is then performed in an ABI 7500 DX Fast Block Real-time PCR machine with the protocol shown in Table 3 below.

TABLE 3

| ABI 7500DX Fast Block real-time PCR protocol | | |
|---|---|---|
| Stage | Time | Temperature |
| UNG | 2 min | 50° C. |
| Denature | 2 min | 93° C. |
| PCR Cycling | 10 sec | 93° C. |
| (45X) | 30 sec | 56° C. |
|  | 20 sec | 72° C. |
| Total Time | 1 hr 10 min |  |

Example 1

This example establishes the criteria for the identification of MRSA and SA using mecA and ldh1 gene-detection. Since mecA and ldh1 are present as single copy genes, in a MRSA genome the respective relative quantities should be the same (1:1) ratio in a case of a single MRSA infection. In case of mixed SA and methicillin-resistant coagulase-negative Staphylococci infection, relative quantities of the respective markers will be different. The Cq value obtained by the real time PCR is indicative of the relative quantity of each marker. Thus by comparing Cq values it is possible to compare relative quantities of the markers. The presence of both SA and mecA markers at the same relative quantity (that is the absolute value of $C_{Q1}$-$C_{Q2}$, a "difference in $C_Q$ called "$\Delta C_Q$ less than 2") is indicative of MRSA; different relative quantities (a difference in $C_Q$ equal or greater than 2) or presence of only the *Staphylococcus aureus*-specific

TABLE 2

| SEQ ID NO: | Component Name | Oligo Sequence | Final 1X | |
|---|---|---|---|---|
| 6 | LDH-L12 | AATAAATCATAAGGT*GA*ACA*TGGTGACACTGAAT | 0.500 | µM |
| 7 | LDH-E4 | AATAAACATAAGCGCTTTGCCCTCAGGACG | 1.260 | µM |
| 8 | MEC-L4 | GTGCGTTAATATTGCCATTATTTTCTAATGCG | 0.500 | µM |
| 9 | MEC-E6 | GGTTACGGACAAGGTGAAATAITGATTAAC | 1.260 | µM |
| 10 | LDH-AP554-5 | MGB-AP554-G*ACATTACT*T*GA*ACAA*CG*CG-EDQ | 0.500 | µM |
| 11 | MEC-FAM3 | MGB-FAM-G*AAAGGATCTGTACTGG*G-EDQ | 0.200 | µM |
| 13 | E6132-642-3 | MGB-AP642-G*AATG*CGGTACGTGGTCC-EDQ | 0.200 | µM |
| 14 | E6132-E | CTCATTTTTTCTACCGGAGATCTTGT | 0.100 | µM |
| 15 | E6132-L | CTGCACGGACCAGTTACTTTACG | 0.300 | µM |
| 16 | dT(8)-AP593 Passive Reference | TTTTTTTT-AP593 | 0.035 | µM |
|  | 2X Tfi PCR Master Mix | NA | 1.00X | |
|  | 10X PCR Enhancer | NA | 1.00X | |
|  | Molecular Biology Grade Water | NA | NA | | gene marker is indicative of SA. It is assumed that the situation with exactly the same quantity of different bacteria in a sample is negligibly rare.

3174 clinical samples were thus tested in a prospective investigational study at three sites. Compared to the reference culture method (latex agglutination and cefoxitin disk susceptibility test after broth enrichment) 92% samples testing positive for MRSA, 96% samples testing positive for SA, and 95% of the negative samples were identified.

Example 2

Figure 2:
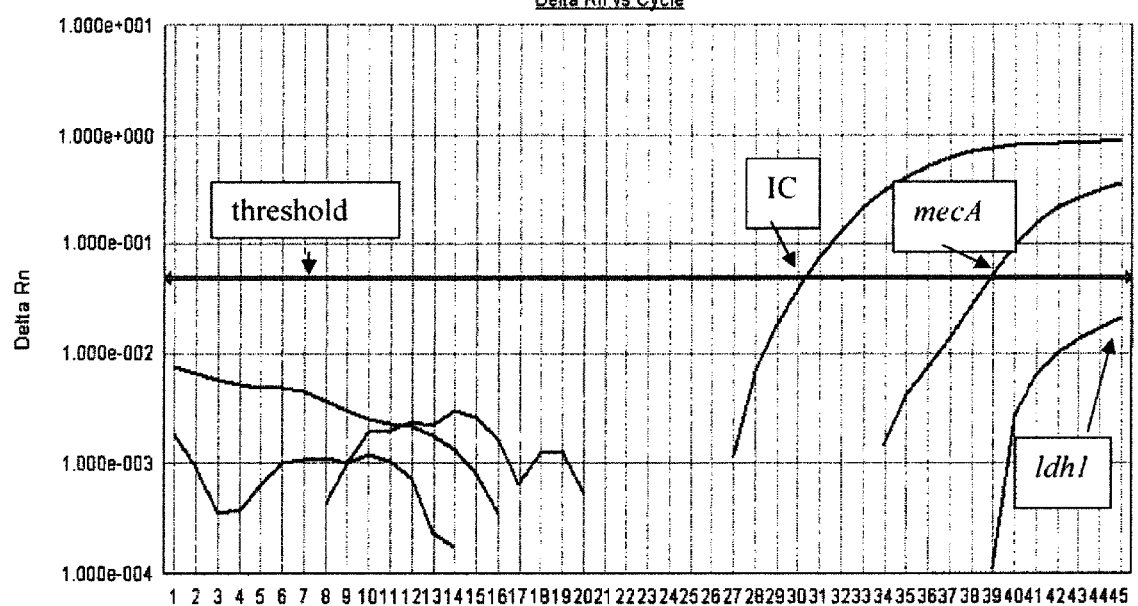
FIG. 2 illustrates the real-time detection of ldh1, mecA, and IC in a SA-negative sample.
Figure 3:
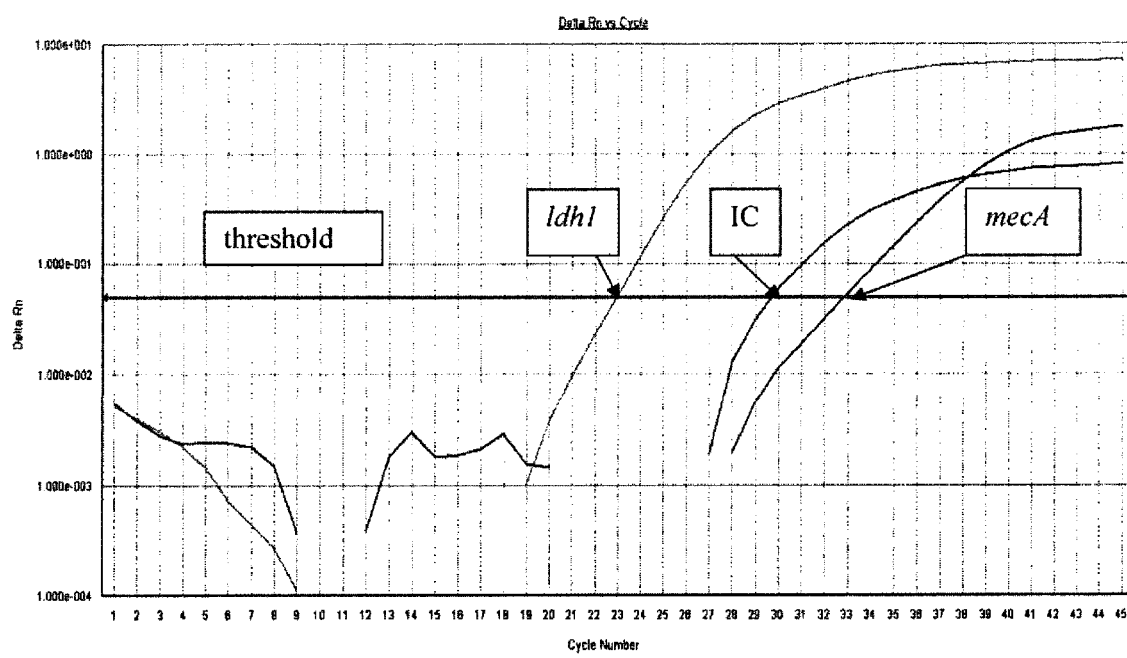
FIG. 3 illustrates the real-time detection of ldh1, mecA, and IC in a SA-positive MRSA-negative sample.

This example illustrates the real-time PCR analysis of a MRSA infection versus mixed infections of MRSA-negative S. aureus and coagulase-negative mecA-positive bacteria (MRCoNS). MRSA positive/IC (FIG. 1). S. aureus-negative/IC (FIG. 2) and MRSA-negative S. aureus-positive/IC-samples (FIG. 3) were run with the reagents and conditions shown above. The similar mecA and ldh1 $C_q$s in FIG. 1 indicate a MRSA infection. Failure of the ldh1 real time curve to cross the threshold in FIG. 2 indicates absence of S. aureus in a sample. The significant difference in $C_q$s between the mecA and ldh1 in FIG. 3 indicates a mixed infection of MRSA-negative S. aureus and coagulase-negative mecA-positive bacteria.

Example 3

This example establishes the criteria for the identification of MRSA and SA using mecA, SCCmec insertion site, and ldh1 gene-detection.

Detection of SCCmec insertion site marker (SCCmec bridge region) is added to account for the situation in which there is approximately the same quantity of different bacteria (MSSA and MRCoNS) in a sample.

Table 4 below shows a comparison of $C_q$s in real-time PCR for SCCmec insertion site, ldh1 and mecA using for a representative panel of clinical samples. The presence of both SA and mecA markers at the same relative quantity ($\Delta C_Q$ less than 2) is indicative of MRSA if that sample is positive for SCCmec bridge region PCR; different relative quantities ($\Delta C_Q$ equal or greater than 2) or presence of only the Staphylococcus aureus-specific gene marker is indicative of SA even if the sample is positive for SCCmec bridge region PCR. SCCmec insertion site primers were previously described (Huletsky, A., et al., J. Clin. Microbiol., 42: 1875-1884 (2004)). The probe used was MGB-AP642-AATTAACACAACCCGCAT-Q (SEQ ID NO: 17).

TABLE 4

| Sample # | LDH1 = $C_{q1}$ | medA = $C_{q2}$ | $\Delta C_q$ $\|C_{q1} - C_{q2}\|$ | SCCmec bridge region | Real-time PCR Result | Culture Result | Concordant? |
|---|---|---|---|---|---|---|---|
| 256 | 23.76 | 24.56 | 0.81 | + | MRSA | MRSA | Yes |
| 261 | 26.53 | 27.13 | 0.60 | − | MSSA | MSSA | Yes |
| 269 | 25.85 | 28.75 | 2.90 | + | MSSA | MSSA | Yes |
| 273 | 32.76 | 38.93 | 6.17 | − | MSSA | MSSA | Yes |
| 282 | 20.33 | 21.11 | 0.77 | + | MRSA | MRSA | Yes |
| 288 | 32.10 | — | NA | − | MSSA | MSSA | Yes |
| 291 | 22.80 | 30.86 | 8.05 | − | MSSA | MSSA | Yes |
| 292 | 25.22 | 24.59 | 0.63 | + | MRSA | MRSA | Yes |
| 298 | 34.19 | 37.66 | 3.47 | − | MSSA | MSSA | Yes |
| 300 | 29.16 | 27.98 | 1.18 | − | MSSA | MSSA | Yes |
| 301 | 32.18 | 32.34 | 0.16 | + | MRSA | MSSA | No |
| 309 | 24.09 | 25.22 | 1.12 | + | MRSA | MRSA | Yes |

TABLE 4-continued

| Sample # | LDH1 = $C_{q1}$ | medA = $C_{q2}$ | $\Delta C_q$ $\|C_{q1} - C_{q2}\|$ | SCCmec bridge region | Real-time PCR Result | Culture Result | Concordant? |
|---|---|---|---|---|---|---|---|
| 337 | 27.78 | 26.02 | 1.76 | − | MSSA | MSSA | Yes |
| 345 | 28.32 | 28.21 | 0.11 | − | MSSA | MSSA | Yes |

As shown in Table 4 above, samples 261, 300, 337 and 345 have approximately the same quantities of mecA and ldh1 markers, but are negative for the SCCmec bridge region marker. This is indicative of a mixed infection (MSSA and MRCoNS) which was confirmed by microbial culture results.

Example 4

This example illustrates the sensitivity of the assay using a freeze-dried culture of organism purchased from ATCC. It also compares the $C_q$s of the real-time PCR of the detection of ldh1 with and without an internal control (IC).

Staphylococcus aureus; subsp. aureus; Strain BAA-1762, LN 593372 47 culture was rehydrated and subcultured as follows. First 0.3 to 0.4 mL of Tryptic Soy Broth Medium (VWR 90000-376) was aseptically added to the freeze-dried material with a Pasteur pipette and mixed well. Then the total mixture was transferred to 5 mL of the same medium in a test tube and was incubated at 37° C. for 24 hours. Bacterial titer was determined making ten fold serial dilutions of the bacterial culture in Tryptic Soy Broth medium. 100 µL of $10^{-5}$, $10^{-6}$ and $10^{-7}$ dilutions were transferred to Trypticase Soy Agar plates and incubated overnight at 37±2° C. Colonies on plates containing 10-200 colonies were counted and the number of colony forming units (CFU)/ml was determined as follows:

CFU/ml=Number of Colonies×10×Dilution Factor

Two sets of seven ten-fold dilutions, covering a range of $10^7$-10 CFU/mL were prepared in ESwab collection media. One mL of the first dilution set was spiked with 10 µL of Internal Control2 (IC2) and the second was not. Both sets were extracted using NucliSENS easyMAG automated extraction system and eluted in 50 µL volume. Three 10 µL replicates of each extracted sample were tested by PCR.

To represent blank pool data, negative samples (SN) (non-simulated ESwab media (M110024)) were separately extracted using the same process, and three 10 µL replicates of each extracted negative sample were also tested by PCR along with CFU samples. Positive target reactions $C_q$s of two sets (with/without IC) were compared.

Table 5 below shows the $C_q$s of serial dilutions of S. aureus cultures detecting ldh1, which is SA marker, in the presence and absence of an internal control (IC).

TABLE 5

| Sample Name | Mean $C_q$s | Δ Mean $C_q$s |
|---|---|---|
| 1e7 No IC2/+IC2 | 13.27/13.28 | 0.01 |
| 1e6 No IC2/+IC2 | 16.88/16.87 | 0.00 |
| 1e5 No IC2/+IC2 | 20.38/20.38 | −0.01 |
| 1e4 No IC2/+IC2 | 23.82/23.83 | −0.01 |
| 1e3 No IC2/+IC2 | 27.13/27.12 | −0.01 |
| 1e2 No IC2/+IC2 | 30.50/30.30 | −0.03 |
| 1e1 No IC2/+IC2 | 33.43/33.37 | 0.10 |

This example shows that the assay readily detects at least 10 CFU/mL and that similar $C_q$s are observed with or without IC.

Example 5

This example illustrates the ability of the assay to detect≥99% of an appropriate number of MRSA strains covering a broad diversity pattern at the relevant clinical load (roughly 100 genome copies/PCR).

Each ATCC *S. aureus* strain (listed in Table 6 below) was plated onto Tryptic Soy Agar plate and incubated at 37° C. for 24 hours. Colony uniformity was verified. One colony from each plate was transferred into a separate (unique for each strain) tube containing 5 mL of Tryptic Soy Broth Medium and let grown overnight at 37° C. 1 mL of the ESwab media was spiked with 10 μL of the overnight culture, and was extracted on EasyMag instrument (Biomerieux) using Generic 2.0.1 protocol and eluted in 50 μL volume. 10 μL from each sample was used in PCR reaction. ldh1 and mecA results were analyzed and summarized in Table 7 below, indicating successful differentiation of mecA-negative MSSA samples from the mecA-positive MRSA samples. As expected, all *S. aureus* strains were positive for SA marker ldh1.

TABLE 6

The list of tested *Staphylococcus aureus* strains (ATCC)

| ATCC Item Number | Strain description | Lot number | mecA | SCC type |
|---|---|---|---|---|
| BAA-1556 (NRS482) | StrainFPR3757; USA300 clone of community-acquired MRSA | 58468651 | Positive | N/A |
| BAA-39 | Strain HUSA304; Hungarian clone of MRSA | 4248847 | Positive | N/A |
| BAA-40 | Strain CPS22; Portuguese clone of MRSA | 57600149 | Positive | N/A |
| 33591 | Strain 328; MRSA | 57882703 | Positive | |
| BAA-1762 | Strain GA217; USA300 MRSA (SCCmec IVb) | 59337247 | Positive | IVb |
| BAA-1720 | MRSA252; Hospital-acquired strain isolated in the United Kingdom | 59049230 | Positive | II |
| 12600 | Strain NCTC 8532, MSSA | 58532124 | Negative | — |
| 25923 | Strain Seattle 1945, MSSA | 58414955 | Negative | — |

TABLE 7

The results of testing *Staphylococcus aureus* strains (ATCC)

| ATCC Item Number | ldh1 gene | mecA gene |
|---|---|---|
| BAA-1556 | Positive | Positive |
| BAA-39 | Positive | Positive |
| BAA-40 | Positive | Positive |
| 33591 | Positive | Positive |
| BAA-1762 | Positive | Positive |
| BAA-1720 | Positive | Positive |
| 12600 | Positive | Negative |
| 25923 | Positive | Negative |

As shown in Tables 6 and 7 the detection of the mecA and ldh1 genes specifically detects MRSA and SA.

Example 6

This example illustrates specificity of the assay. It was evaluated by testing for cross-reactivity to species phylogenetically related to *S. aureus*, pathogenic microorganisms and to microorganisms commonly present in normal nasal microflora. The test panel (Table 8) consisted of 17 viral, 3 fungal, 1 mycoplasma, and 41 bacterial species. The microorganisms were tested as cultures in concentrations of $1 \times 10^6$ CFU $1 \times 10^5$ PFU)/swab. In addition human cells in a concentration of $10^6$ cells/mL were tested. Human cells and all tested species were found negative for MRSA and SA. The analytical specificity was 100%.

TABLE 8

Species Tested for Cross-Reactivity and Microbial Interference

| *Staphylococci* Species | Other Organisms | Viruses |
|---|---|---|
| CoNS* | *Acinetobacter haemolyticus*, | Adenovirus Type 1, |
| *Staphylococcus arlettae*, | *Bacillus cereus, Bordetella pertussis, Citrobacter freundii,* | Adenovirus Type 7A, Human *coronavirus* (229E), |
| Staphylococcus capitis, | *Citrobacter koseri,* | Human *coronavirus* (OC43), |
| *Staphylococcus carnosus*, | *Corynebacterium aquaticum, Corynebacterium bovis,* | *Cytomegalovirus*, Coxsackievirus Type A21, |
| *Staphylococcus chromogenes*, | *Corynebacterium flavescens, Corynebacterium genitalium,* | Epstein Barr Virus, Human influenza virus A, |
| *Staphylococcus equorum*, | *Enterobacter aerogenes, Enterococcus faecalis,* | Human influenza virus B, Human parainfluenza Type 2, |
| *Staphylococcus felis*, | *Enterococcus faecium,* | Human parainfluenza Type 3, |
| *Staphylococcus gallinarum*, | *Enterococcus flavescens, Enterococcus gallinarum,* | *Human metapneumovirus* 3 Type B1, |
| *Staphylococcus hominis* subsp. *hominis*, | *Enterococcus hiraem, Escherichia coli*, ESBL | Measles, Mumps virus, |
| *Staphylococcus kloosii*, | producer, *Klebsiella oxytoca,* | *Respiratory syncytial virus* |
| *Staphylococcus lentus*, | *Klebsiella pneumoniae*, ESBL | Type B, |
| *Staphylococcus puivereri*, | producer, *Listeria monocytogenes, Moraxella* | *Rhinovirus* Type 1A |
| *Staphylococcus simulans*, | *catarrhalis, Pasteurella aerogenes, Proteus mirabilis,* | |
| *Staphylococcus warneri* MSCoPS* | *Proteus vulgaris, Pseudomonas aeruginosa, Salmonella* | |
| *Staphylococcus delphini*, | *typhimurium, Serratia* | |

TABLE 8-continued

Species Tested for Cross-Reactivity and Microbial Interference

| *Staphylococci* Species | Other Organisms | Viruses |
|---|---|---|
| MSCoNS* | marcescens, Shigella sonnei, | |
| *Staphylococcus epidermidis*, | *Streptococcus mitis*, | |
| *Staphylococcus xylosus* | *Streptococcus salivarius*, | |
| MRCoNS* | *Yersinia enterocolitica*, | |
| *Staphylococcus epidermidis* | *Candida albicans, Candida glabrata, Cryptococcus neoformans, Lactobacillus* | |
| CoPS* | *acidophilus, Legionella* | |
| *Staphylococcus hyicus*, | *pneumophila, Mycobacterium* | |
| *Staphylococcus intermedius* | *tuberculosis avirulent,* | |
| | *Mycoplasma pneumoniae,* | |
| | *Neisseria meningitides,* | |
| | *Streptococcus mutans,* | |
| | *Streptococcus pneumoniae,* | |
| | *Streptococcus pyogenes, Homo sapiens*, Human Cells HT1080 | |

*CoNS: coagulase-negative *Staphylococci*,
MSCoPS: methicillin susceptible coagulase positive *Staphylococci*,
MSCoNS: methicillin susceptible coagulase negative *Staphylococci*,
MRCoNS: methicillin resistant coagulase negative *Staphylococci*,
CoPS: coagulase positive *Staphylococci*

Example 7

This example illustrates the successful detection of MRSA isolate harboring mecA gene and LGA251 MRSA isolate which has a different gene from the majority of MRSA methicillin-resistance genes and is called mecA$_{LGA251}$. PCR amplification is performed as disclosed in Table 2, with conditions as described in Table 3 except that primers SEQ ID NOs: 20 to 22 were added representing the primers and probes for the PCR amplification of mecA$_{LGA251}$ (Table 9).

TABLE 9

Primer and probe sequences for mecA$_{LGA251}$ detection

| SEQ ID NO | Component Name | Oligo Sequence | Final 1X |
|---|---|---|---|
| 20 | LGA-L12 | CTCGTCAGAAT*T*AATTGGACCCAC | 0.500 µM |
| 21 | LGA-E5 | GCCGTGTTTATCCATTGAACGAAGOA | 1.260 µM |
| 22 | LGA-FAM11 | MGB-FAM-G*TAAAAGGTGTACTGTTGC-EDQ | 0.200 µM |

Figure 4:
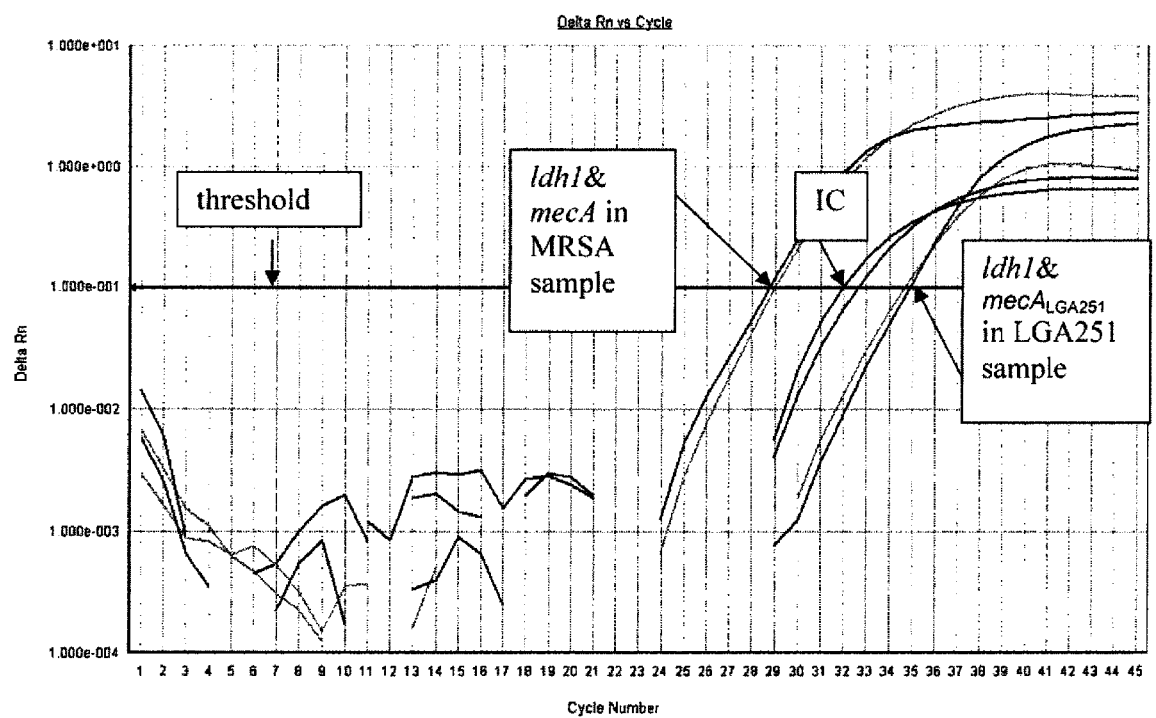
FIG. 4 illustrates the real-time detection of mecA, $mecA_{LGA251}$ ldh1 and IC in MRSA-positive and LGA251-positive samples.

The results are shown in FIG. 4: for both MRSA-positive and LGA251-positive samples the $C_q$s for ldh1 and mecA (mecA$_{LGA251}$) are similar.

Example 8

This example demonstrates result interpretation for a computer-based method and system described herein using Excel "if" functionality for nasal swab samples processed using a bioMerieux easyMag extraction and a Applied Biosystems® 7500 Fast Dx Real-time PCR instrument.

Ct (cycle threshold, also referred to as Cq) is defined as the number of cycles required for the fluorescent signal to cross the threshold (i.e. exceed the background level). The SA (ldh1) cycle threshold is defined as $C_{T1}$, the mecA cycle threshold is defined as $C_{T2}$, and the IC control threshold is defined as CT.

Situations 1-5 defined below demonstrate the chosen Ct values and their assigned result.

Situation 1: IF $C_{T1}$>35.0 AND $C_{T2}$>35.0 AND IC $C_T$<34.0, then the result is "MRSA-negative/SA-negative."
Situation 2: IF $C_{T1}$>35.0 AND $C_{T2}$>35.0 AND IC $C_T$≥34.0, then the result is "Invalid."
Situation 3: IF $C_{T1}$≤35.0 AND $C_{T2}$≤35.0 AND |$C_{T1}$-$C_{T2}$|<2, then the result is "MRSA-positive."
Situation 4: IF $C_{T1}$≤35.0, AND |$C_{T1}$-$C_{T2}$|≥2, then the result is "MRSA-negative/SA-positive."
Situation 5: IF $C_{T2}$>35.0 AND $C_{T2}$≤35.0, then the result is "MRSA-negative/SA-negative."

Table 10 below shows collected clinical sample data in the form of collected Cts in Columns B, C, and D. The situation summaries below Table 10 show examples of the calls generated by Excel "if" functions using selected clinical sample results representative of four of the situations set forth above. E2, E7, E20, and E4 refer to cell numbers corresponding to sample calls shown in column E.

TABLE 10

| | A Sample ID# | B IC | C ldh1 | D mecA | E MRSA/SA ELITe MGB testing (performed by Epoch) (Algorithm) |
|---|---|---|---|---|---|
| 1 | | | | | |
| 2 | 1 | 30.0174 | 50 | 37.7672 | NEG |
| 3 | 2 | 30.1315 | 50 | 36.3186 | NEG |
| 4 | 3 | 30.009 | 37.8131 | 33.0587 | NEG |

TABLE 10-continued

| 1 | A<br>Sample<br>ID# | B<br>IC | C<br>Idh1 | D<br>mecA | E<br>MRSA/SA<br>ELITe MGB<br>testing<br>(performed by<br>Epoch)<br>(Algorithm) |
|---|---|---|---|---|---|
| 5 | 4 | 30.0331 | 38.3301 | 38.3669 | NEG |
| 6 | 5 | 30.1328 | 50 | 31.525 | NEG |
| 7 | 6 | 30.2983 | 23.7551 | 24.5647 | MRSA |
| 8 | 7 | 30.0692 | 50 | 36.3243 | NEG |
| 9 | 8 | 30.1117 | 35.5751 | 35.7661 | NEG |
| 10 | 9 | 30.1551 | 50 | 32.1061 | NEG |
| 11 | 10 | 30.1809 | 50 | 28.3299 | NEG |
| 12 | 11 | 30.1308 | 26.5344 | 27.1298 | MRSA |
| 13 | 12 | 29.9252 | 50 | 33.0466 | NEG |
| 14 | 13 | 30.0645 | 35.4711 | 33.3906 | NEG |
| 15 | 14 | 29.9879 | 50 | 50 | NEG |
| 16 | 15 | 31.1726 | 37.0951 | 36.048 | NEG |
| 17 | 16 | 30.3026 | 50 | 36.0029 | NEG |
| 18 | 17 | 30.6207 | 50 | 50 | NEG |
| 19 | 18 | 30.3318 | 50 | 30.5635 | NEG |
| 20 | 19 | 30.246 | 25.8525 | 28.7516 | SA |

Situation 1:
E2=IF(AND(C2<=35.05,ABS(C2-D2)<2,D2<=35.05),
"MRSA",IF(AND(C2<=35.05,ABS(C2-D2)>=2),"SA",
"NEG")) Result Call: "MRSA-Negative/SA-Negative"
Situation 3:
E7=IF(AND(C7<=35.05,ABS(C7-D7) 2,D7=35.05),
"MRSA",IF(AND(C7<=35.05,ABS(C7-D7)>2),"SA",
"NEG")) Result Call: "MRSA-Positive"
Situation 4:
E20==IF(AND(C20<=35.05,ABS(C20-D20)<2,
D20<=35.05),"MRSA",IF(AND(C20<=35 0.05,ABS(C20-
D20)>=2), "SA","NEG")) Result Call: "MRSA-Negative/
SA-Positive"
Situation 5:
E4=IF(AND(C4<=35.05,ABS(C4-D4)<2,D4<=35.05),
"MRSA",IF(AND(C4<=35.05,ABS(C4-D4)>=2),"SA",
"NEG")) Result Call: "MRSA-Negative/SA-Negative"

It should be noted that an example of Situation 2 is not provided due to the absence of an invalid result in Table 10.

REFERENCES

U.S. Patent Documents

U.S. Pat. Nos. 3,194,805; 3,128,179; 3,996,345; 4,351,760; 4,683,195; 4,683,202; 4,965,188; 5,187,288; 5,188,934; 5,227,487, 5,248,782; 5,304,645; 5,433,896; 5,442,045; 5,492,806; 5,525,464; 5,556,752; 5,556,959; 5,583,236; 5,808,044; 5,852,191; 5,986,086; 5,994,056; 6,020,481; 6,127,121; 6,156,507; 6,162,931; 6,171,785; 6,180,295; 6,221,604; 6,569,627; 6,727,356; 6,790,945; 6,946,267; 6,949,367; 7,348,146; 7,671,218; 7,767,834; 7,838,221; RE 38,416
U.S. Patent Publication No. 2005/0118623

International Patent Documents

International Patent Publication No. WO 03/023357, WO 02/062816, WO 92/10588 and WO 96/17957
EP Patent Nos. 1408366, 1314734

OTHER PUBLICATIONS

Ausubel, et al., CURRENT PROTOCOLS IN MOLECULAR BIOLOGY, John Wiley & Sons (1987, 1988, 1989, 1990, 1991, 1992, 1993, 1994, 1995, 1996)
Bengtsson et al., Nucl. Acids Res., 31: e45 (2003)
Blanc et al., J. Clin. Microbiol., 49: 722-724 (2011)
Bolli et al., Nucleic Acids Res., 24:4660-4667 (1996)
Boucher et al., CID., 51 (supplement2): S183S197 (2010)
Brown et al., Pharmacoeconomics, 28: 567-575 (2010)
Chen et al., Nucleic Acids Res., 23:2661-2668 (1995)
Dieffenbach et al. (eds.), PCR Primer: A Laboratory Manual, Cold Spring Harbor Laboratory Press (2003)
Eckstein (ed.), OLIGONUCLEOTIDES AND ANALOGUES: A PRACTICAL APPROACH, IRL Press (1991)
Fieser and Fieser, REAGENTS FOR ORGANIC SYNTHESIS, Volumes 1 to 17, Wiley, US (1995)
Gait (ed.), OLIGONUCLEOTIDE SYNTHESIS: A PRACTICAL APPROACH, IRL Press (1984)
Geiger et al., Nature 359:859-861 (1992)
Gemmel et al., J. Antimicrob. Chemother., 57: 589-608 (2006)
Hartman & Tomasz, J. Bacteriol., 158: 513-516 (1984)
Haugland et al., Handbook of Fluorescent Probes and Research Chemicals, Sixth Ed., Molecular Probes, Eugene, Ore. (1996)
Hiramatsu et al., Int. J. Me. Microbiol., 292:67-74 (2002)
Hirschberg et al., Biochemistry 37:10381-10385 (1998)
Huletsky et al., J. Clin. Microbiol., 42: 1875-1884 (2004)
Innis et al., eds, PCR Protocols: A Guide to Methods and Applications, 1990
Kolman et al., BMC Res. Notes, 3; 110 (2010)
Krasoviskii and Bolotin, Organic Luminescent Materials, VCH Publishers, NY. (1988)
March et al., ADVANCED ORGANIC CHEMISTRY—Reactions, Mechanisms and Structures, 4th ed., John Wiley & Sons, New York, N.Y. (1992)
McPherson et al., PCR Basics, 2000
Mullis et al., Cold Spring Harb. Symp. Quant. Biol., 51 Pt 1:263-273 (1986)
Nielsen et al., Science, 254:1497-1500 (1991)
Palissa et al., Z. Chem., 27:216 (1987)
Richardson et al., Science, 319: 1672 (2008)
Rossney et al., J. Clin. Microbiol., 46:3285-3290 (2008)
Sambrook, Fritsch & Maniatis, MOLECULAR CLONING: A LABORATORY MANUAL, Second Edition, Cold Spring Harbor Laboratory Press (1989)
Sherlock et al., Clin. Microbiol. Infect. 16:955-959 (2010)
Singh et al., Chem. Comm., 455-456 (1998)
Smith et al., J. Chem. Soc. Perkin Trans. 2:1195-1204 (1993)
Stevenson J et al., J Clin Microbiol., 43: 2391-8 (2005)
Warren et al., J. Clin Microbiol., 42: 5578-5581 (2004)
Wengel, Acc. Chem. Res., 32:301-310 (1998)
Whitaker, et al., Anal. Biochem. 207:267-279 (1992)
Wittwer et al. (eds.), Rapid Cycle Real-time PCR Methods and Applications: Quantification, Springer-Verlag (2004)
Wong et al. J. Clin. Microbiol., 48: 3525-3531 (2010)
Zolliger, Color Chemistry, $2^{nd}$ Edition, VCH Publishers, NY (1991)

What is claimed:

1. A method for detecting a methicillin-resistant *Staphylococcus aureus* ("MRSA") in a sample containing nucleic acids, comprising:
   amplifying the nucleic acids in the sample; and
   detecting nucleic acids in the sample comprising amplified genes, wherein the presence of amplified genes consisting of mecA and ldh1 genes in approximately 1:1 ratio indicates the presence of methicillin-resistant *Staphylococcus aureus*, and wherein a difference in concentration of the amplified genes consisting of amplified mecA and amplified ldh1 genes indicates a mixed infection of *Staphylococcus aureus* and a coagulase-negative carrier of mecA in the sample,
   wherein the step of amplifying the nucleic acids in the sample comprises:
   (a) contacting the sample with a first primer and a second primer having the formula:

$$5'-(X)_nY-3' \qquad (I),$$

wherein n is 0 or 1, wherein when n is 1 X represents a 5' portion of the primers that is non-complementary to the ldh1 gene and X is about 3-30 nucleotides in length, wherein Y represents a 3' portion of the primers that is complementary to the ldh1 gene, and wherein Y in the first primer comprises SEQ ID NO:4, GGT*GA*ACA*TGGTGACACTGAAT, wherein T* is 5-(4-hydroxy-but-1-ynyl)-1H-pyrimidine-2,4-dione and A* is 4-(4,6-Diamino-1H-pyrazolo[3,4-d]pyrimidin-3-yl)-but-3-yn-1-ol;
   (b) contacting the sample after step (a) with a third primer and a fourth primer having the formula:

$$5'-(X)_nY'-3' \qquad (I),$$

wherein n is 0 or 1, wherein when n is 1 X represents a 5' portion of the primers that is non-complementary to the mecA gene and X is about 3-30 nucleotides in length, and wherein Y' represents a 3' portion of the primers that is complementary to the mecA gene; and
   (c) incubating the sample following steps (a) and (b) under conditions sufficient to amplify the ldh1 and mecA genes.

2. The method of claim 1, wherein the amplified ldh1 gene comprises SEQ ID NO: 1 and the amplified mecA gene comprises SEQ ID NO:2.

3. The method of claim 1, wherein the amplifying is continuously monitored during the detecting step.

4. The method of claim 3, further comprising the step of calculating real time concentrations of amplified mecA and ldh1 genes.

5. The method of claim 1, wherein the amplified mecA and ldh1 genes are detected by hybridization to mecA or ldh1 specific probes.

6. The method of claim 5, wherein the probes are fluorescence-generating probes.

7. The method of claim 6, wherein the ldh1 specific fluorescence-generating probe comprises SEQ ID NO:10, 5'-Ra-G*ACATTACT*T*GA*ACAA*CG-Rb 5', wherein Ra is $(M)_a$-Fl or $(M)_a$-Q, Rb is $(M)_a$-Fl or $(M)_a$-Q, M is a minor groove binder, a is 0 or 1, Fl is a fluorophore with emission wavelength between about 400 and 900 nm, Q is a non-fluorescent quencher, T* is 5-(4-hydroxy-but-1-ynyl)-1H-pyrimidine-2,4-dione, A* is 4, (4,6-Diamino-1H-pyrazolo[3,4-d]pyrimidin-3-yl)-but-3-yn-1-ol, and G* is 6-amino-1H-pyrazolo[3,4-d]pyrimidin-4(5H)-one, wherein one of Ra and Rb comprises a fluorophore and the other comprises a quencher, and wherein the quencher allows quenching of fluorescence when the probe is unhybridized.

8. The method of claim 6, wherein the mecA specific fluorescence-generating probe comprises SEQ ID NO:11, 5'-Ra-G*AAAGGATCTGTACTGG*G-Rb 5', wherein Ra is $(M)_a$-Fl or $(M)_a$-Q, Rb is $(M)_a$-Fl or $(M)_a$-Q, M is a minor groove binder, a is 0 or 1, Fl is a fluorophore with emission wavelength between about 400 and 900 nm, Q is a non-fluorescent quencher, and G* is 6-amino-1H-pyrazolo[3,4-d]pyrimidin-4(5H)-one, wherein one of Ra and Rb comprises a fluorophore and the other comprises a quencher, and wherein the quencher allows quenching of fluorescence when the probe is unhybridized.

9. The method of claim 1, wherein the primers are fluorescence-generating primers.

10. The method of claim 1, further comprising the step of detecting nucleic acids in the sample comprising at least one amplified SCCmec integration site or bridge region.

11. The method of claim 1, further comprising the step of detecting nucleic acids in the sample comprising at least one amplified *Staphylococcus aureus* ("SA") specific gene in addition to ldh1.

12. The method of claim 1, wherein the first primer comprises SEQ ID NO:6, AATAAATCATAAGGT*GA*ACA*TGGTGACACTGAAT, having an underlined first sequence that is non-complementary to the ldh1 gene, wherein T* is 5-(4-hydroxy-but-1-ynyl)-1H-pyrimidine-2,4-dione and A* is 4-(4,6-Diamino-1H-pyrazolo[3,4-d]pyrimidin-3-yl)-but-3-yn-1-ol, and wherein the second primer comprises SEQ ID NO:7, AATAAATCATAAGCGCTTTGCCCTCAGGACG, having an underlined second sequence that is non-complementary to the ldh1 gene.

13. The method of claim 1, wherein the third primer comprises SEQ ID NO:8, GTGCGTTAATATTGCCATTATTTTCTAATGCG, wherein n is 0, and wherein the fourth primer comprises SEQ ID NO:9, GGTTACGGACAAGGTGAAATAITGATTAACC, wherein n is 0 and I is 3-alkynyl-1H-pyrazolo[3,4-d]pyrimidin-4(5H)-one.

14. A method for detecting a methicillin-resistant *Staphylococcus aureus* ("MRSA") in a sample containing nucleic acids, comprising:
amplifying the nucleic acids in the sample; and
detecting nucleic acids in the sample comprising amplified genes, wherein the presence of amplified genes consisting of mecA and Idh1 genes in approximately 1:1 ratio indicates the presence of methicillin-resistant *Staphylococcus aureus*, and wherein a difference in concentration of the amplified genes consisting of amplified mecA and amplified Idh1 genes indicates a mixed infection of *Staphylococcus aureus* and a coagulase-negative carrier of mecA in the sample,
wherein the step of amplifying the nucleic acids in the sample comprises:
(a) contacting the sample with a first primer and a second primer having the formula:
5'-(X)nY-3', wherein n is 1 and X represents a 5' portion of the primers that is non-complementary to the Idh1 gene and X is about 3-30 nucleotides in length, wherein Y represents a 3' portion of the primers that is complementary to the Idh1 gene, wherein the first primer comprises SEQ ID NO:6 AATAAATCATAAGGT*GA*ACA*TGGTGACACTGAAT, having an underlined first sequence that is non-complementary to the Idh1 gene, wherein T* is 5-(4-hydroxy-but-1-ynyl)-1H-pyrimidine-2,4-dione and A* is 4-(4,6-Diamino-1H-pyrazolo[3,4-d]pyrimidin-3-yl)-but-3-yn-1-ol, and wherein the second primer comprises SEQ ID NO:7 AATAAATCATAAGCGCTTTGCCCTCAGGACG, having an underlined second sequence that is non-complementary to the Idh1 gene;
(b) contacting the sample after step (a) with a third primer and a fourth primer having the formula: 5'-(X)nY'-3', wherein n is 0 or 1, wherein when n is 1 X represents a 5' portion of the primers that is non-complementary to the mecA gene and X is about 3-30 nucleotides in length, and wherein Y' represents a 3' portion of the primers that is complementary to the mecA gene; and
(c) incubating the sample following steps (a) and (b) under conditions sufficient to amplify the Idh1 and mecA genes.

15. A method for detecting a methicillin-resistant *Staphylococcus aureus* ("MRSA") in a sample containing nucleic acids, comprising:
amplifying the nucleic acids in the sample; and
detecting nucleic acids in the sample comprising amplified genes, wherein the presence of amplified genes consisting of mecA and Idh1 genes in approximately 1:1 ratio indicates the presence of methicillin-resistant *Staphylococcus aureus*, and wherein a difference in concentration of the amplified genes consisting of amplified mecA and amplified Idh1 genes indicates a mixed infection of *Staphylococcus aureus* and a coagulase-negative carrier of mecA in the sample, wherein the step of amplifying the nucleic acids in the sample comprises:
(a) contacting the sample with a first primer and a second primer having the formula: 5'-(X)nY-3', wherein n is 0 or 1, wherein when n is 1 X represents a 5' portion of the primers that is non-complementary to the Idh1 gene and X is about 3-30 nucleotides in length, wherein Y represents a 3' portion of the primers that is complementary to the Idh1 gene;
(b) contacting the sample after step (a) with a third primer and a fourth primer complementary to the mecA gene, wherein the third primer comprises SEQ ID NO:8 GTGCGTTAATATTGCCATTATTTTCTAATGCG,
and wherein the fourth primer comprises SEQ ID NO: 9 GGTTACGGACAAGGTGAAATAITGATTAACC, wherein I is 3-alkynyl-1H-pyrazolo[3,4-d]pyrimidin-4(5H)-one; and
(c) incubating the sample following steps (a) and (b) under conditions sufficient to amplify the Idh1 and mecA genes.

16. A method for detecting a methicillin-resistant *Staphylococcus aureus* ("MRSA") in a sample containing nucleic acids, comprising:
amplifying the nucleic acids in the sample; and
detecting nucleic acids in the sample comprising amplified genes, wherein the presence of amplified genes consisting of mecA and Idh1 genes in approximately 1:1 ratio indicates the presence of methicillin-resistant *Staphylococcus aureus*, and wherein a difference in concentration of the amplified genes consisting of amplified mecA and amplified Idh1 genes indicates a mixed infection of *Staphylococcus aureus* and a coagulase-negative carrier of mecA in the sample, wherein the step of amplifying the nucleic acids in the sample comprises:
(a) contacting the sample with a first primer and a second primer having the formula: 5'-(X)nY-3', wherein n is 0 or 1, wherein when n is 1 X represents a 5' portion of the primers that is non-complementary to the Idh1 gene and X is about 3-30 nucleotides in length, wherein Y represents a 3' portion of the primers that is complementary to the Idh1 gene;
(b) contacting the sample after step (a) with a third primer and a fourth primer having the formula: 5'-(X)nY'-3', wherein n is 0 or 1, wherein when n is 1 X represents a 5' portion of the primers that is non-complementary to the mecA gene and X is about 3-30 nucleotides in length, and wherein Y' represents a 3' portion of the primers that is complementary to the mecA gene; and
(c) incubating the sample following steps (a) and (b) under conditions sufficient to amplify the Idh1 and mecA genes, wherein the amplified mecA and Idh1 genes are detected by hybridization to a mecA specific probe and a Idh1 specific probe, and wherein the Idh1 specific fluorescence-generating probe comprises SEQ ID NO: 10 5'-Ra G*ACATTACT*T*GA*ACAA*CG-Rb 5', wherein Ra is $(M)_a$-Fl or $(M)_a$-Q, Rb is $(M)_a$-Fl or $(M)_a$-Q, M is a minor groove binder, a is 0 or 1, Fl is a fluorophore with emission wavelength between about 400 and 900 nm, Q is a non-fluorescent quencher, T* is 5-(4-hydroxy-but-1-ynyl)-1H-pyrimidine-2,4-dione, A* is 4, (4,6-Diamino-1H-pyrazolo[3,4-d]pyrimidin-3-yl)-but-3-yn-1-ol, and G* is 6-amino-1H-pyrazolo[3,4-d]pyrimidin-4(5H)-one, wherein one of Ra and Rb comprises a fluorophore and the other comprises a quencher, and wherein the quencher allows quenching of fluorescence when the probe is unhybridized.

17. A method for detecting a methicillin-resistant *Staphylococcus aureus* ("MRSA") in a sample containing nucleic acids, comprising:

amplifying the nucleic acids in the sample; and detecting nucleic acids in the sample comprising amplified genes, wherein the presence of amplified genes consisting of mecA and ldh1 genes in approximately 1:1 ratio indicates the presence of methicillin-resistant *Staphylococcus aureus*, and wherein a difference in concentration of the amplified genes consisting of amplified mecA and amplified ldh1 genes indicates a mixed infection of *Staphylococcus aureus* and a coagulase-negative carrier of mecA in the sample, wherein the step of amplifying the nucleic acids in the sample comprises:

(a) contacting the sample with a first primer and a second primer having the formula: 5'-(X)nY-3', wherein n is 0 or 1, wherein when n is 1 X represents a 5' portion of the primers that is non-complementary to the ldh1 gene and X is about 3-30 nucleotides in length, wherein Y represents a 3' portion of the primers that is complementary to the ldh1 gene;

(b) contacting the sample after step (a) with a third primer and a fourth primer having the formula: 5'-(X)nY'-3', wherein n is 0 or 1, wherein when n is 1 X represents a 5' portion of the primers that is non-complementary to the mecA gene and X is about 3-30 nucleotides in length, and wherein Y' represents a 3' portion of the primers that is complementary to the mecA gene; and (c) incubating the sample following steps (a) and (b) under conditions sufficient to amplify the ldh1 and mecA genes, wherein the amplified mecA and ldh1 genes are detected by hybridization to a mecA specific probe and a ldh1 specific probe, and wherein the mecA specific fluorescence generating probe comprises SEQ ID NO: 11 5'-Ra-G*AAAGGATCTGTACTGG*G-Rb 5', wherein Ra is $(M)_a$-Fl or $(M)_a$-Q, Rb is $(M)_a$-Fl or $(M)_a$-Q, M is a minor groove binder, a is 0 or 1, Fl is a fluorophore with emission wavelength between about 400 and 900 nm, Q is a non-fluorescent quencher, and G* is 6-amino-1H-pyrazolo[3,4-d]pyrimidin-4(5H)-one, wherein one of Ra and Rb comprises a fluorophore and the other comprises a quencher, and wherein the quencher allows quenching of fluorescence when the probe is unhybridized.

* * * * *

SEQUENCE LISTING

<160> NUMBER OF SEQ ID NOS: 29

<210> SEQ ID NO 1
<211> LENGTH: 100
<212> TYPE: DNA
<213> ORGANISM: Staphylococcus aureus

<400> SEQUENCE: 1
ggtgaacatg gtgacactga attaccagta tggtcacacg ctaatattgc gggtcaacct      60
ttgaagacat tacttgaaca acgtcctgag ggcaaagcgc                          100

<210> SEQ ID NO 2
<211> LENGTH: 88
<212> TYPE: DNA
<213> ORGANISM: Staphylococcus aureus

<400> SEQUENCE: 2
gtgcgttaat attgccatta ttttctaatg cgctatagat tgaaaggatc tgtactgggt      60
taatcagtat ttcaccttgt ccgtaacc                                        88

<210> SEQ ID NO 3
<211> LENGTH: 12
<212> TYPE: DNA
<213> ORGANISM: Artificial Sequence
<220> FEATURE:
<223> OTHER INFORMATION: 5' sequence portion of flap primer
      non-complementary to ldh1 or mecA sequence

<400> SEQUENCE: 3
aataaatcat aa                                                         12

<210> SEQ ID NO 4
<211> LENGTH: 22
<212> TYPE: DNA
<213> ORGANISM: Artificial Sequence
<220> FEATURE:
<223> OTHER INFORMATION: 3' Y portion of first flap primer
<220> FEATURE:
<221> NAME/KEY: misc_feature
<222> LOCATION: (3)..(3)
<223> OTHER INFORMATION: n is 5-(4-hydroxy-but-1-ynyl)-1H-pyrimidine-
      2,4-dione (SUPER T)
<220> FEATURE:
<221> NAME/KEY: misc_feature
<222> LOCATION: (5)..(5)
<223> OTHER INFORMATION: n is 4-(4,6-Diamino-1H-
      pyrazolo[3,4-d]pyrimidin-3-yl)-but-3-yn-1-ol (SUPER A)
<220> FEATURE:
<221> NAME/KEY: misc_feature
<222> LOCATION: (8)..(8)
<223> OTHER INFORMATION: n is 4-(4,6-Diamino-1H-
      pyrazolo[3,4-d]pyrimidin-3-yl)-but-3-yn-1-ol (SUPER A)

<400> SEQUENCE: 4
ggngnacntg gtgacactga at                                              22

<210> SEQ ID NO 5
<211> LENGTH: 19
<212> TYPE: DNA
<213> ORGANISM: Artificial Sequence
<220> FEATURE:
<223> OTHER INFORMATION: 3' Y portion of second flap primer

<400> SEQUENCE: 5
gcgctttgcc ctcaggacg                                                  19

```
<210> SEQ ID NO 6
<211> LENGTH: 34
<212> TYPE: DNA
<213> ORGANISM: Artificial Sequence
<220> FEATURE:
<223> OTHER INFORMATION: First flap primer sequence
<220> FEATURE:
<221> NAME/KEY: misc_feature
<222> LOCATION: (15)..(15)
<223> OTHER INFORMATION: n is SUPER T
<220> FEATURE:
<221> NAME/KEY: misc_feature
<222> LOCATION: (17)..(17)
<223> OTHER INFORMATION: n is SUPER A
<220> FEATURE:
<221> NAME/KEY: misc_feature
<222> LOCATION: (20)..(20)
<223> OTHER INFORMATION: n is SUPER A

<400> SEQUENCE: 6
aataaatcat aaggngnacn tggtgacact gaat                        34

<210> SEQ ID NO 7
<211> LENGTH: 31
<212> TYPE: DNA
<213> ORGANISM: Artificial Sequence
<220> FEATURE:
<223> OTHER INFORMATION: Second flap primer sequence

<400> SEQUENCE: 7
aataaatcat aagcgctttg ccctcaggac g                           31

<210> SEQ ID NO 8
<211> LENGTH: 32
<212> TYPE: DNA
<213> ORGANISM: Artificial Sequence
<220> FEATURE:
<223> OTHER INFORMATION: Third flap mecA primer sequence

<400> SEQUENCE: 8
gtgcgttaat attgccatta ttttctaatg cg                          32

<210> SEQ ID NO 9
<211> LENGTH: 31
<212> TYPE: DNA
<213> ORGANISM: Artificial Sequence
<220> FEATURE:
<223> OTHER INFORMATION: Fourth flap mecA primer sequence
<220> FEATURE:
<221> NAME/KEY: misc_feature
<222> LOCATION: (22)..(22)
<223> OTHER INFORMATION: n is 3-alkynyl-1H-pyrazolo[3,4-d]pyrimidin-
      4(5H)-one (Super Inosine)

<400> SEQUENCE: 9
ggttacggac aaggtgaaat antgattaac c                           31

<210> SEQ ID NO 10
<211> LENGTH: 18
<212> TYPE: DNA
<213> ORGANISM: Artificial Sequence
<220> FEATURE:
<223> OTHER INFORMATION: Sequence of probe for ldh1 gene
<220> FEATURE:
<221> NAME/KEY: misc_feature
<222> LOCATION: (1)..(1)
<223> OTHER INFORMATION: n is 6-amino-1H-pyrazolo[3,4-d]pyrimidin-4(5H)-
      one (SUPER G) conjugated to a fluorophore or quencher, with or
      without a minor groove binder
<220> FEATURE:
<221> NAME/KEY: misc_feature
```

```
<222> LOCATION: (9)..(9)
<223> OTHER INFORMATION: n is SUPER T
<220> FEATURE:
<221> NAME/KEY: misc_feature
<222> LOCATION: (10)..(10)
<223> OTHER INFORMATION: n is SUPER T
<220> FEATURE:
<221> NAME/KEY: misc_feature
<222> LOCATION: (12)..(12)
<223> OTHER INFORMATION: n is SUPER A
<220> FEATURE:
<221> NAME/KEY: misc_feature
<222> LOCATION: (16)..(16)
<223> OTHER INFORMATION: n is SUPER A
<220> FEATURE:
<221> NAME/KEY: misc_feature
<222> LOCATION: (18)..(18)
<223> OTHER INFORMATION: n is G conjugated to a fluorophore or quencher,
      with or without a minor groove binder

<400> SEQUENCE: 10
nacattacnn gnacancn                                                 18

<210> SEQ ID NO 11
<211> LENGTH: 18
<212> TYPE: DNA
<213> ORGANISM: Artificial Sequence
<220> FEATURE:
<223> OTHER INFORMATION: Sequence of probe for mecA gene
<220> FEATURE:
<221> NAME/KEY: misc_feature
<222> LOCATION: (1)..(1)
<223> OTHER INFORMATION: n is SUPER G conjugated to a fluorophore or
      quencher, with or without a minor groove binder
<220> FEATURE:
<221> NAME/KEY: misc_feature
<222> LOCATION: (17)..(17)
<223> OTHER INFORMATION: n is SUPER G
<220> FEATURE:
<221> NAME/KEY: misc_feature
<222> LOCATION: (18)..(18)
<223> OTHER INFORMATION: n is G conjugated to a fluorophore or quencher,
      with or without a minor groove binder

<400> SEQUENCE: 11
naaaggatct gtactgnn                                                 18

<210> SEQ ID NO 12
<211> LENGTH: 68
<212> TYPE: DNA
<213> ORGANISM: Artificial Sequence
<220> FEATURE:
<223> OTHER INFORMATION: Sequence of nucleic acid control fragment

<400> SEQUENCE: 12
ctgcacggac cagttacttt acggaccacg taccgcattg gtacaagatc tccggtagaa   60
aaaatgag                                                            68

<210> SEQ ID NO 13
<211> LENGTH: 18
<212> TYPE: DNA
<213> ORGANISM: Artificial Sequence
<220> FEATURE:
<223> OTHER INFORMATION: Sequence for control probe
<220> FEATURE:
<221> NAME/KEY: misc_feature
<222> LOCATION: (1)..(1)
<223> OTHER INFORMATION: n is SUPER G conjugated to fluorophore or
      quencher, with or without a minor groove binder
<220> FEATURE:
<221> NAME/KEY: misc_feature
<222> LOCATION: (5)..(5)
```

<223> OTHER INFORMATION: n is SUPER G
<220> FEATURE:
<221> NAME/KEY: misc_feature
<222> LOCATION: (18)..(18)
<223> OTHER INFORMATION: n is C conjugated to fluorophore or quencher,
      with or without a minor groove binder

<400> SEQUENCE: 13
naatncggta cgtggtcn                                                     18

<210> SEQ ID NO 14
<211> LENGTH: 23
<212> TYPE: DNA
<213> ORGANISM: Artificial Sequence
<220> FEATURE:
<223> OTHER INFORMATION: Sequence of first control primer

<400> SEQUENCE: 14
ctgcacggac cagttacttt acg                                               23

<210> SEQ ID NO 15
<211> LENGTH: 26
<212> TYPE: DNA
<213> ORGANISM: Artificial Sequence
<220> FEATURE:
<223> OTHER INFORMATION: Sequence of second control primer

<400> SEQUENCE: 15
ctcatttttt ctaccggaga tcttgt                                            26

<210> SEQ ID NO 16
<211> LENGTH: 8
<212> TYPE: DNA
<213> ORGANISM: Artificial Sequence
<220> FEATURE:
<223> OTHER INFORMATION: Sequence for dT8-AP593 passive reference
      control
<220> FEATURE:
<221> NAME/KEY: misc_feature
<222> LOCATION: (8)..(8)
<223> OTHER INFORMATION: n is T conjugated to AP593

<400> SEQUENCE: 16 tttttttn                                                                8

<210> SEQ ID NO 17
<211> LENGTH: 18
<212> TYPE: DNA
<213> ORGANISM: Artificial Sequence
<220> FEATURE:
<223> OTHER INFORMATION: Sequence of probe for detection of SCCmec
      insertion site
<220> FEATURE:
<221> NAME/KEY: misc_feature
<222> LOCATION: (1)..(1)
<223> OTHER INFORMATION: n is A conjugated to minor groove binder and
      AP642
<220> FEATURE:
<221> NAME/KEY: misc_feature
<222> LOCATION: (18)..(18)
<223> OTHER INFORMATION: n is T conjugated to quencher

<400> SEQUENCE: 17
nattaacaca acccgcan                                                     18

<210> SEQ ID NO 18
<211> LENGTH: 529
<212> TYPE: DNA
<213> ORGANISM: Artificial Sequence

```
<220> FEATURE:
<223> OTHER INFORMATION: Sequence of plasmic insert of control nucleic
      acid

<400> SEQUENCE: 18
acgtagcgtc gatgctcaaa ttattggtga acatggtgac actgaattac cagtatggtc      60
acacgctaat attgcgggtc aacctttgaa gacattactt gaacaacgtc ctgagggcaa     120
agcgcaaatt gaacaaattt ttgttcaaac acgtgatgca gcatatgaca ttattcaagc     180
taaaggtgcc acttattatg gtgttgcaat gggattagct agaagctatc tgcagaattc     240 gccctttac gacttgttgc ataccatcag ttaatagatt gatattttct ttggaaataa      300
tatttttctt ccaaactttg tttttcgtgt cttttaataa gtgaggtgcg ttaatattgc     360
cattattttc taatgcgcta tagattgaaa ggatctgtac tgggttaatc agtatttcac     420
cttgtccgta acctgaatca gctaataata tttcattatc taaattttg tttgaaattt      480 gagcattata aaatggataa tcacttggta tatcttcacc aacacctag               529

<210> SEQ ID NO 19
<211> LENGTH: 71
<212> TYPE: DNA
<213> ORGANISM: Artificial Sequence
<220> FEATURE:
<223> OTHER INFORMATION: Sequence of control nucleic acid used as mecA
      LGA251 positive control

<400> SEQUENCE: 19
ctcgtcagaa ttaattggac ccacataacc taaaggtgt actgttgctt cgttcaatgg       60
ataaacacgg c                                                          71

<210> SEQ ID NO 20
<211> LENGTH: 24
<212> TYPE: DNA
<213> ORGANISM: Artificial Sequence
<220> FEATURE:
<223> OTHER INFORMATION: Sequence of first mecA LGA251 primer
<220> FEATURE:
<221> NAME/KEY: misc_feature
<222> LOCATION: (11)..(11)
<223> OTHER INFORMATION: n is SUPER T
<220> FEATURE:
<221> NAME/KEY: misc_feature
<222> LOCATION: (12)..(12)
<223> OTHER INFORMATION: n is SUPER T

<400> SEQUENCE: 20
ctcgtcagaa nnaattggac ccac                                            24

<210> SEQ ID NO 21
<211> LENGTH: 26
<212> TYPE: DNA
<213> ORGANISM: Artificial Sequence
<220> FEATURE:
<223> OTHER INFORMATION: Sequence of second mecA LGA251 primer

<400> SEQUENCE: 21
gccgtgttta tccattgaac gaagca                                          26

<210> SEQ ID NO 22
<211> LENGTH: 19
<212> TYPE: DNA
<213> ORGANISM: Artificial Sequence
<220> FEATURE:
<223> OTHER INFORMATION: Sequence of probe for mecA LGA251 detection
<220> FEATURE:
```

```
<221> NAME/KEY: misc_feature
<222> LOCATION: (1)..(1)
<223> OTHER INFORMATION: n is SUPER G conjugated to fluorophore and
      minor groove binder
<220> FEATURE:
<221> NAME/KEY: misc_feature
<222> LOCATION: (19)..(19)
<223> OTHER INFORMATION: n is C conjugated to quencher

<400> SEQUENCE: 22
ntaaaaggtg tactgttgn                                               19

<210> SEQ ID NO 23
<211> LENGTH: 31
<212> TYPE: DNA
<213> ORGANISM: Artificial Sequence
<220> FEATURE:
<223> OTHER INFORMATION: Sequence of alternate primer for amplification
      of mecA LGA251 gene

<400> SEQUENCE: 23
ggatatggcc aaggcgagat actagtaaac c                                 31

<210> SEQ ID NO 24
<211> LENGTH: 38
<212> TYPE: DNA
<213> ORGANISM: Artificial Sequence
<220> FEATURE:
<223> OTHER INFORMATION: Sequence of alternate primer for amplification
      of mecA LGA251 gene

<400> SEQUENCE: 24
gaggattttg tatatttccg ttattttcta aagcactg                          38

<210> SEQ ID NO 25
<211> LENGTH: 35
<212> TYPE: DNA
<213> ORGANISM: Artificial Sequence
<220> FEATURE:
<223> OTHER INFORMATION: Sequence of alternate primer for amplication of
      mecA LGA251 gene

<400> SEQUENCE: 25
aataaatcat aagggttgaa cctggtgatg tagtg                             35

<210> SEQ ID NO 26
<211> LENGTH: 37
<212> TYPE: DNA
<213> ORGANISM: Artificial Sequence
<220> FEATURE:
<223> OTHER INFORMATION: Sequence of alternate primer for amplication of
      mecA LGA251 gene
<220> FEATURE:
<221> NAME/KEY: misc_feature
<222> LOCATION: (28)..(28)
<223> OTHER INFORMATION: n is SUPER T
<220> FEATURE:
<221> NAME/KEY: misc_feature
<222> LOCATION: (29)..(29)
<223> OTHER INFORMATION: n is SUPER T
<220> FEATURE:
<221> NAME/KEY: misc_feature
<222> LOCATION: (30)..(30)
<223> OTHER INFORMATION: n is SUPER T

<400> SEQUENCE: 26
aataaatcat aacaataaaa aagagccnnn gctcaac                           37

<210> SEQ ID NO 27
```

```
<211> LENGTH: 19
<212> TYPE: DNA
<213> ORGANISM: Artificial Sequence
<220> FEATURE:
<223> OTHER INFORMATION: Sequence of alternate probe for detection of
      mecA LGA251 gene
<220> FEATURE:
<221> NAME/KEY: misc_feature
<222> LOCATION: (1)..(1)
<223> OTHER INFORMATION: n is SUPER G conjugated to fluorophore or
      quencher, with or without a minor groove binder
<220> FEATURE:
<221> NAME/KEY: misc_feature
<222> LOCATION: (12)..(12)
<223> OTHER INFORMATION: n is SUPER A
<220> FEATURE:
<221> NAME/KEY: misc_feature
<222> LOCATION: (19)..(19)
<223> OTHER INFORMATION: n is C conjugated to fluorophore or quencher,
      with or without a minor groove binder

<400> SEQUENCE: 27
ntaaaaggtg tnctgttgn                                                   19

<210> SEQ ID NO 28
<211> LENGTH: 17
<212> TYPE: DNA
<213> ORGANISM: Artificial Sequence
<220> FEATURE:
<223> OTHER INFORMATION: Sequence of alternate probe for detection of
      mecA LGA251 gene
<220> FEATURE:
<221> NAME/KEY: misc_feature
<222> LOCATION: (1)..(1)
<223> OTHER INFORMATION: n is SUPER G conjugated to fluorophore or
      quencher, with or without a minor groove binder
<220> FEATURE:
<221> NAME/KEY: misc_feature
<222> LOCATION: (8)..(8)
<223> OTHER INFORMATION: n is SUPER T
<220> FEATURE:
<221> NAME/KEY: misc_feature
<222> LOCATION: (9)..(9)
<223> OTHER INFORMATION: n is SUPER T
<220> FEATURE:
<221> NAME/KEY: misc_feature
<222> LOCATION: (10)..(10)
<223> OTHER INFORMATION: n is SUPER T
<220> FEATURE:
<221> NAME/KEY: misc_feature
<222> LOCATION: (13)..(13)
<223> OTHER INFORMATION: n is SUPER A
<220> FEATURE:
<221> NAME/KEY: misc_feature
<222> LOCATION: (15)..(15)
<223> OTHER INFORMATION: n is SUPER A
<220> FEATURE:
<221> NAME/KEY: misc_feature
<222> LOCATION: (17)..(17)
<223> OTHER INFORMATION: n is G conjugated to fluorophore or quencher,
      with or without a minor groove binder

<400> SEQUENCE: 28
nataaaannn gtntngn                                                     17

<210> SEQ ID NO 29
<211> LENGTH: 17
<212> TYPE: DNA
<213> ORGANISM: Artificial Sequence
<220> FEATURE:
<223> OTHER INFORMATION: Sequence of alternate probe for detection of
      mecA LGA251 gene
<220> FEATURE:
<221> NAME/KEY: misc_feature
<222> LOCATION: (1)..(1)
```

-continued

```
<223> OTHER INFORMATION: n is A conjugated to fluorophore or quencher,
      with or without a minor groove binder
<220> FEATURE:
<221> NAME/KEY: misc_feature
<222> LOCATION: (4)..(4)
<223> OTHER INFORMATION: n is SUPER T
<220> FEATURE:
<221> NAME/KEY: misc_feature
<222> LOCATION: (5)..(5)
<223> OTHER INFORMATION: n is SUPER T
<220> FEATURE:
<221> NAME/KEY: misc_feature
<222> LOCATION: (6)..(6)
<223> OTHER INFORMATION: n is SUPER T
<220> FEATURE:
<221> NAME/KEY: misc_feature
<222> LOCATION: (17)..(17)
<223> OTHER INFORMATION: n is C conjugated to fluorophore or quencher,
      with or without a minor groove binder

<400> SEQUENCE: 29
naannncaaa tcactan                                                   17
```